United States Patent [19]

Sato et al.

[11] Patent Number: 5,461,048
[45] Date of Patent: Oct. 24, 1995

[54] TRICYCLIC COMPOUNDS HAVING CHOLECYSTOKININ ANTAGONIST ACTIVITY

[75] Inventors: Yoshinari Sato, Takaishi; Teruaki Matuo, Osaka; Takatomo Ogahara, Minoo, all of Japan

[73] Assignee: Fujisawa Pharmaceutical Co., Ltd., Osaka, Japan

[21] Appl. No.: 351,164

[22] Filed: Nov. 30, 1994

Related U.S. Application Data

[62] Division of Ser. No. 77,607, Jul. 23, 1993, Pat. No. 5,401,737, which is a division of Ser. No. 919,265, Jul. 27, 1992, Pat. No. 5,248,679, which is a division of Ser. No. 612,955, Nov. 15, 1990, Pat. No. 5,155,101, which is a division of Ser. No. 396,124, Aug. 21, 1989, Pat. No. 4,981,847.

[30] Foreign Application Priority Data

Sep. 9, 1988 [GB] United Kingdom ............... 8821257
Dec. 15, 1988 [GB] United Kingdom ............... 8829265

[51] Int. Cl.$^6$ ................... A61K 31/55; C07D 487/06
[52] U.S. Cl. ................... 514/211; 514/220; 540/556; 540/559; 540/560
[58] Field of Search ................... 514/211, 220, 514/556; 540/559, 560

[56] References Cited

U.S. PATENT DOCUMENTS

| 4,981,847 | 1/1991 | Sato et al. | 514/211 |
| 5,155,101 | 10/1992 | Sato et al. | 514/211 |
| 5,248,679 | 9/1993 | Sato et al. | 514/220 |

*Primary Examiner*—Yogendra N. Gupta
*Attorney, Agent, or Firm*—Oblon, Spivak, McClelland, Maier & Neustadt

[57] ABSTRACT

The invention relates to novel cholecystokinin antagonists of the formula

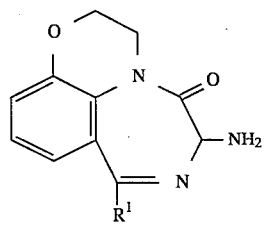

wherein $R^1$ is aryl or substituted aryl, and a pharmaceutically acceptable salt thereof useful as cholecystokinin antagonists.

5 Claims, No Drawings

TRICYCLIC COMPOUNDS HAVING CHOLECYSTOKININ ANTAGONIST ACTIVITY

This is a division of application Ser. No. 08/077,607 filed on Jul. 23, 1993, now U.S. Pat. No. 5,401,737 which was a division of application Ser. No. 07/919,265, filed on Jul. 27, 1992, now U.S. Pat. No. 5,248,679, which was a division of application Ser. No. 07/612,955, filed on Nov. 15, 1990, now U.S. Pat. No. 5,155,101, which was a division of application Ser. No. 07/396,124, filed on Aug. 21, 1989, now U.S. Pat. No. 4,981,847.

This invention relates to new tricyclic compounds and pharmaceutically acceptable salts thereof.

More particularly, it relates to new tricyclic compounds and pharmaceutically acceptable salts thereof which are cholecystokinin (CCK) antagonists and therefore useful as therapeutical and/or preventive agents for emesis, pancreatitis, satiety and appetite control, pain control, insulinoma, gastroparesis, carcinoma of pancreas, gallbladder disease (e.g. acute cholecystitis, calculus, etc.), disorders associated with intestinal smooth muscle hyperactivity (e.g. irritable bowel syndrome, sphincter spasm, etc.), hyperinsulinemia, dyspepsia, nausea, etc.

The tricyclic compounds of this invention can be represented by the following formula (I):

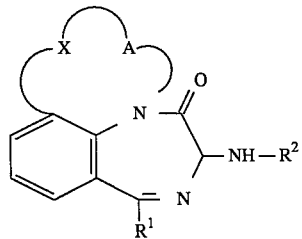

wherein
$R^1$ is aryl which may have suitable substituent(s),
X is —O— or

(in which $R^3$ is hydrogen or lower alkyl),
A is a bond or lower alkylene which may have lower alkyl group(s), and
$R^2$ is hydrogen or an acyl group.

According to the present invention, the new tricyclic compounds (I) can be prepared by the processes which are illustrated in the following scheme.

Process 1

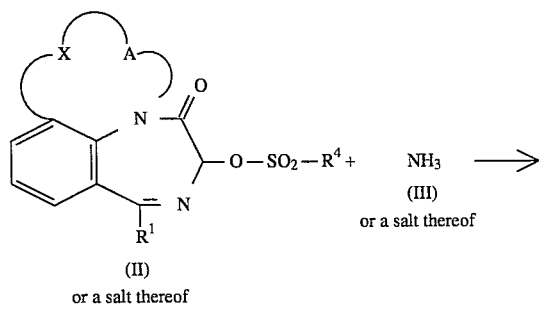

Process 2

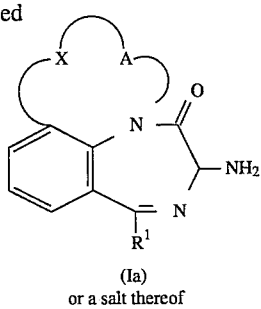

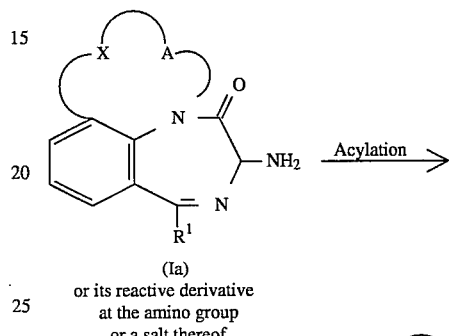

Process 3

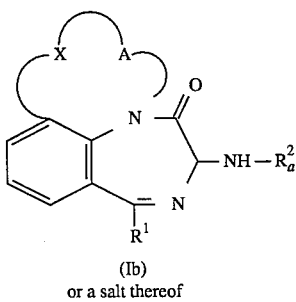

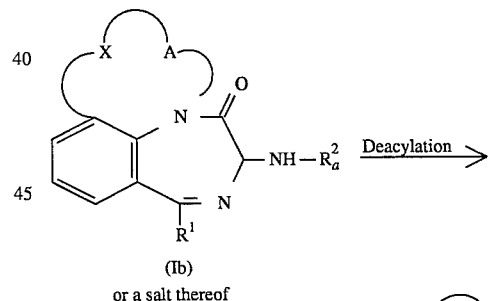

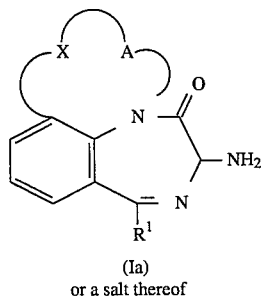

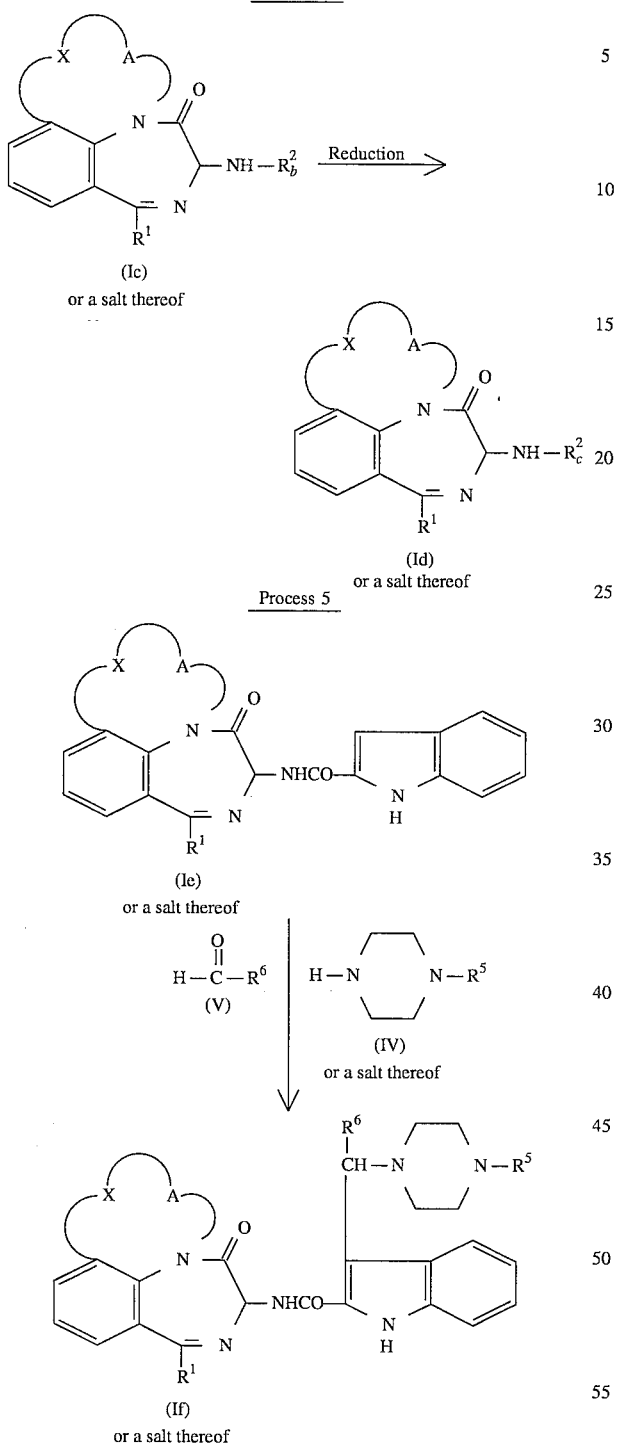
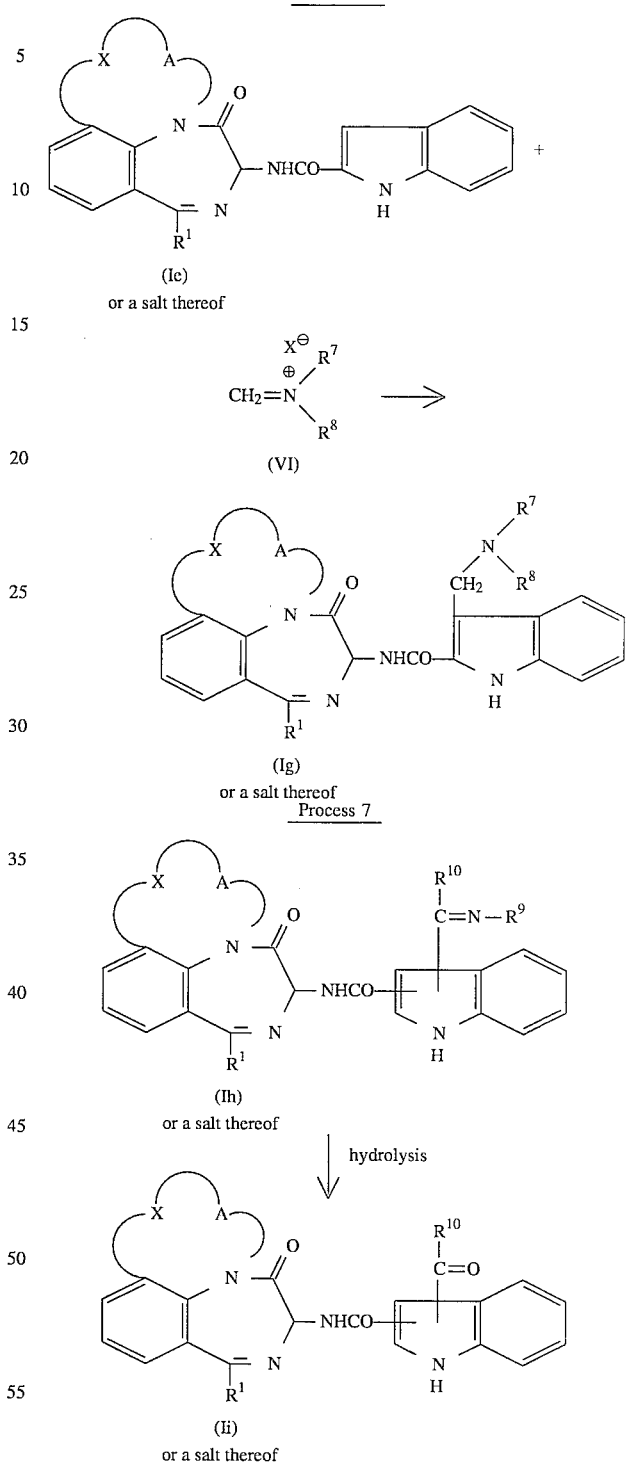

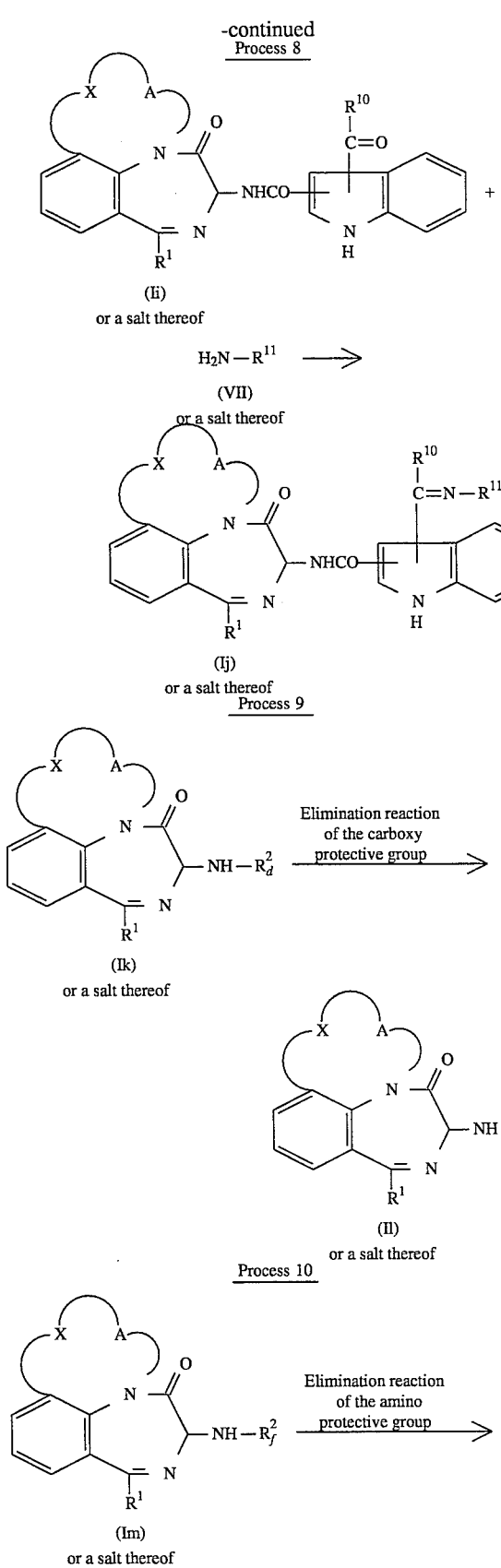
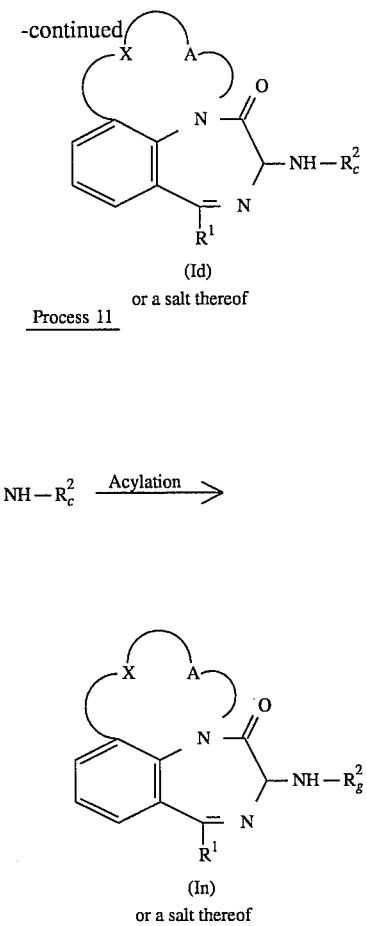

wherein

R¹, A and X are each as defined above, $R^4$ is lower alkyl, $R_a^2$ is an acyl group, $R_b^2$ is acyl having a nitro group, $R_c^2$ is acyl having an amino group, $R^5$ is hydrogen or hydroxy(lower)alkyl, $R^6$ is hydrogen or $(C_1-C_5)$alkyl, $R^7$ is lower alkyl, $R^8$ is lower alkyl, X is halogen, $R^9$ is aryl, $R^{10}$ is hydrogen or $(C_1-C_5)$alkyl, $R^{11}$ is hydroxy or lower alkyl, $R_d^2$ is acyl having a protected carboxy group, $R_e^2$ is acyl having a carboxy group, $R_f^2$ is acyl having a protected amino group, $R_g^2$ is acyl having an acylamino group.

The starting compound (II) is novel and can be prepared by the following processes.

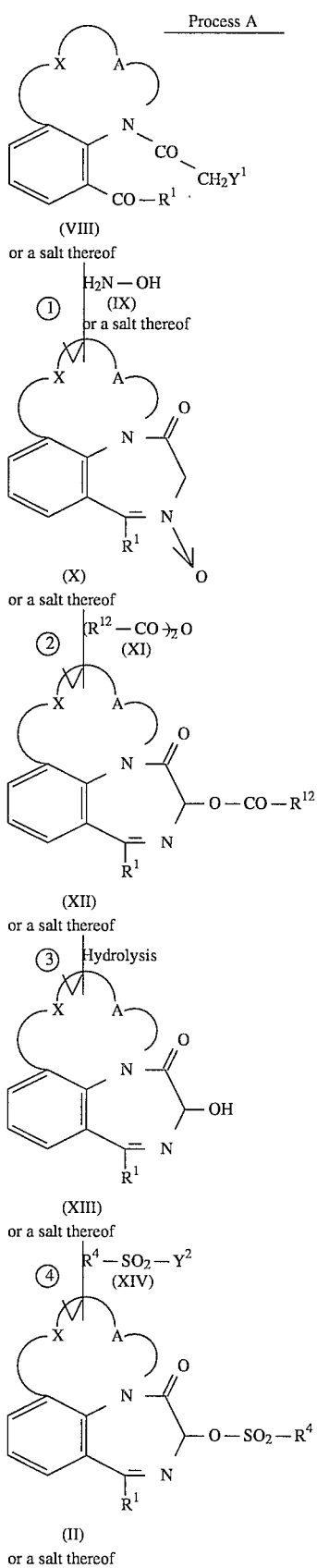

wherein $R^1$, $R^4$, A and X are each as defined above,
$Y^1$ is halogen,
$R^{12}$ is lower alkyl, and
$Y^2$ is halogen.

The starting compound (VIII) or a salt thereof can be prepared by the methods disclosed in the Preparations 1 and 2 described later or similar manners thereto.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

Suitable "aryl" for $R^1$ may include phenyl, naphthyl and the like, and said aryl group may have one or more (preferably 1 to 3) suitable substituent(s) such as halogen, amino, lower alkoxy, mono(or di or tri)halo(lower)alkyl or the like.

Suitable "halogen" and "halogen moiety" in the term "mono(or di or tri)halo(lower)alkyl" may include chlorine, bromine, fluorine and iodine.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "lower alkylene" may include straight one having 1 to 6 carbon atom(s), such as methylene, ethylene, trimethylene, tetramethylene, pentamethylene or hexamethylene, preferably one having 1 to 3 carbon atom(s), and said lower alkylene group may have one or more (preferably 1 to 3) lower alkyl group(s).

Suitable "lower alkyl" and "lower alkyl moiety" in the term "mono(or di or tri)halo(lower)alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "acyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Alliphatic acyl such as lower or higher alkanoyl (e.g. formyl, acetyl, propanoyl, butanoyl, 2-methylpropanoyl, pentanoyl, 2,2-dimethylpropanoyl, hexanoyl heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g. methoxycarbonyl, ethoxycarbonyl, t-butoxycarbonyl, t-pentyloxycarbonyl, heptyloxycarbonyl, etc.); lower or higher alkanesulfonyl (e.g. methanesulfonyl, ethanesulfonyl, etc.); lower or higher alkoxysulfonyl (e.g. methoxysulfonyl, ethoxysulfonyl, etc.); or the like;

Aromatic acyl such as aroyl (e.g. benzoyl, toluoyl, naphthoyl, etc.);

ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.), etc.];

ar(lower)alkenoyl [e.g. phenyl(lower)alkenoyl (e. g. phenylpropenoyl, phenylbutenoyl, phenylmethacryloyl, phenylpentenoyl, phenylhenxenoyl, etc.), naphthyl(lower)alkenoyl (e.g. naphthylpropenoyl, napthylbutenoyl, naphthylpentenoyl, etc.), etc.];

ar(lower)alkoxycarbonyl [e.g. phenyl(lower)alkoxycarbonyl (e.g. benzyloxycarbonyl, etc.), etc.]; aryloxycarbonyl (e.g. phenoxycarbonyl, napthyloxycarbonyl, etc.); aryloxy(lower)alkanoyl (e.g. phenoxyacetyl, phenoxypropionyl, etc.); arylcarbamoyl (e.g. phenylcarbamoyl, etc.); arylthiocarbamoyl (e.g. phenylthiocarbamoyl, etc.); arylglyoxyloyl (e.g. phenylglyoxyloyl, naphthylglyoxyloyl, etc.); arenesulfonyl (e.g. benzenesulfonyl, p-toluenesulfonyl, etc.); or the like;

Heterocyclic acyl such as heterocycliccarbonyl; heterocyclic (lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.); heterocyclic(lower)alkenoyl (e.g. heterocyclicpropenoyl, heterocyclicbutenoyl, heterocyclicpentenoyl, heterocyclichexenoyl, etc.); heterocyclicglyoxyloyl (e.g. thiazolylglyoxyloyl, thienylglyoxyloyl, etc.); or the like; in which suitable heterocyclic moiety in the terms "heterocycliccarbonyl" , "heterocyclic(lower)alkanoyl", heterocyclic(lower)alkenoyl and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3,-triazolyl, etc.), tetrazolyl (e.g. 1H-tetrazolyl, 2H-tetrazolyl, etc.), etc.; saturated 3 to 8-membered (more preferably 5 or 6-membered)heteromonocyclic group containing 1 to 4 nitrogen atom(s), for example pyrrolidinyl, imidazolidinyl, piperidino, piperazinyl, etc.; unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.; unsaturated 3 to 8-membered (more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.; saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.; saturated 3 to 8-membered (more preferably 5 or 6-membered) heteromonocyclic group containing 1 to 2 sulfur atom(s) and 1 to 3 nitrogen atom(s), for example, thiazolidinyl, etc.; unsaturated 3 to 8-membered (more preferably 5 or 6-membered) heteromonocyclic group containing 1 to 2 sulfur atom(s), for example, thienyl, dihydrodithiinyl, dihydrodithionyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6-membered) heteromonocyclic group containing an oxygen atom, for example, furyl, etc.; unsaturated 3 to 8-membered (more preferably 5 or 6-membered)heteromonocyclic group containing an oxygen atom and 1 to 2 sulfur atom(s), for example, dihydrooxathiinyl, etc.; unsaturated condensed heterocyclic group containing 1 to 2 sulfur atom(s), for example, benzothienyl, benzodithiinyl, etc.; unsaturated condensed heterocyclic group containing an oxygen atom and 1 to 2 sulfur atom(s), for example, benzoxathiinyl, etc. and the like. The acyl moiety as stated above may have one to ten, same or different, suitable substituent(s) such as halogen (e.g. fluorine, chlorine, bromine or iodine), hydroxy, nitro, lower alkyl (e.g. methyl, ethyl, propyl, isopropyl, butyl, isobutyl, t-butyl, pentyl, hexyl, etc.); amino, protected amino, heterocyclic(lower)alkylamino wherein heterocyclic and lower alkyl moieties can be referred to the ones as mentioned above, lower alkoxy (e.g. methoxy, ethoxy, propoxy, butoxy, t-butoxy, pentyloxy, hexyloxy, etc.), carboxy, protected carboxy, N,N-di(lower)alkylamino(lower)alkyl (e.g. N,N-dimethylaminomethyl, N,N-diethylaminomethyl, N,N-dipropylaminomethyl, N,N-dimethylaminoethyl, N,N-diethylaminoethyl, N,N-dipropylaminoethyl, N,N-dimethylaminopropyl, N,N-diethylaminopropyl, N,N-dipropylaminopropyl, N,N-dibutylaminomethyl, N,N-dipentylaminomethyl, N,N-dihexylaminomethyl, etc.), hydroxyimino(lower)alkyl (e.g. hydroxyiminomethyl, hydroxyiminoethyl, hydroxyiminopropyl, hydroxyiminobutyl, hydroxyiminopentyl, hydroxyiminohexyl, etc.), arylimino(lower)alkyl [e.g. phenylimino(lower)alkyl (e.g. phenyliminomethyl, phenyliminoethyl, phenyliminopropyl, phenyliminobutyl, phenyliminopentyl, phenyliminohexyl, etc.), etc.], acyl such as lower alkanoyl (e.g. formyl, acetyl, propanoyl, butanoyl, pentanoyl, hexanoyl, etc.), hydroxy(lower)alkylheterocyclic(lower)alkyl wherein lower alkyl and heterocyclic moieties can be referred to the ones as mentioned above, mono(or di or tri)halo(lower)alkyl, arylamino(e.g. phenylamino, etc.), or the like. Suitable "protected amino" may include acylamino and the like. Suitable "acyl moiety" in the term "acylamino" can be referred to the ones as mentioned above.

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy (lower)-alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl 2-oxo-1,3-dioxol-4-yl) (lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)-phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like. Preferred embodiments of the object compound (I) are as follows.

$R^1$ is phenyl which may have halogen, X is —O— or

(in which $R^3$ is hydrogen or lower alkyl),

A is a bond or lower alkylene which may have lower alkyl, $R^2$ is hydrogen;

ar(lower)alkenoyl which may have 1 to 3 substituent(s) selected from the group consisting of halogen, hydroxy, nitro, lower alkyl, lower alkoxy, amino, protected amino and heterocyclic(lower)alkylamino [more preferably phenyl(lower)alkenoyl which may have one or two substituent(s) selected from the group consisting of halogen, hydroxy, nitro, lower alkyl, lower alkoxy, amino, acylamino and imidazolyl(lower)-alkylamino, most preferably phenyl(lower)alkenoyl which may have one or two substituent(s) selected from the group consisting of halogen, hydroxy, nitro, lower alkyl, lower alkoxy, amino, lower alkanoylamino and imidazolyl(lower)alkylamino];

heterocyclic(lower)alkenoyl which may have carboxy or protected carboxy [more preferably indolyl (lower)alkenoyl which may have carboxy or protected carboxy; imidazolyl(lower)alkenoyl; or quinolyl(lower)alkenoyl, most preferably indolyl(lower)alkenoyl which may have carboxy or esterified carboxy; imidazolyl(lower)alkenoyl; or quinolyl(lower)alkenoyl];

heterocycliccarbonyl which may have N,N-di(lower)alkylamino(lower)alkyl, hydroxyimino(lower)alkyl, arylimino(lower)alkyl, acyl or hydroxy(lower)alkylheterocyclic(lower)alkyl [more preferably indolylcarbonyl which may have N,N-di(lower)alkylamino(lower)alkyl, hydroxyimino(lower)alkyl, phenylimino(lower)alkyl, lower alkanoyl or hydroxy(lower)alkylpiperazinyl(lower)alkyl; quinolylcarbonyl; or indolinylcarbonyl]; aroyl which may have 1 to 3 substituent(s) selected from the group consisting of halogen, amino and mono (or di or tri)halo(lower)alkyl [more preferably benzoyl which may have one or two substituent(s) selected from the group consisting of halogen, amino and mono (or di or tri)halo(lower)alkyl];

arylcarbamoyl which may have halogen or lower alkoxy [more preferably phenylcarbamoyl which may have halogen or lower alkoxy];

arylamino(lower)alkanoyl [more preferably phenylamino(lower)alkanoyl]; or ar(lower)alkanoyl which may have amino or protected amino [more preferably phenyl(lower)alkanoyl which may have amino or acylamino, most preferably phenyl(lower)alkanoyl which may have amino, lower alkoxycarbonylamino or phenyl-thiocarbamoylamino], The processes for preparing the object compound (I) of the present invention are explained in detail in the following.

Process 1

The compound (Ia) or a salt thereof can be prepared by reacting the compound (II) or a salt thereof with the compound (III) or a salt thereof.

This reaction is usually carried out in a solvent such as alcohol (e.g., methanol, ethanol, etc.), benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

Process 2

The compound (Ib) or a salt thereof can be prepared by subjecting the compound (Ia) or its reactive derivative at the amino group or a salt thereof to acylation reaction.

Suitable acylating agent to be used in the present acylation reaction may include the compound of the formula:

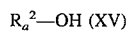

(wherein $R_a^2$ is acyl) or its reactive derivative or a salt thereof.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as N,O-bis(trimethylsilyl)acetamide, N-trimethylsilylacetamide or the like; a derivative formed by the reaction of the compound (Ia) with phosphorus trichloride or phosgene, and the like.

Suitable salts of the compound (Ia) and (XV) can be referred to the ones as exemplified for the compound (I).

Suitable reactive derivative of the compound (XV) may include an acid halide, an acid anhydride, an activated amide, an activated ester, isocyanate, and the like. The suitable example may be an acid chloride an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl

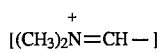

ester, vinyl ester, propargyl ester, p-nitrophenyl ester, 2,4-dinitrophenyl ester, trichlorophenyl ester, pentachlorophenyl ester, mesylphenyl ester, penylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); substituted or unsubstituted aryl isocyanate; substituted or unsubstituted aryl isothiocyanate; and the like. These reactive derivatives can optionally be selected from them according to the kind of the compound (XV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (XV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxasolium salt; 2-ethyl-5-(m-sulfophenyl)-isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling to heating.

Process 3

The compound (Ia) or a salt thereof can be prepared by subjecting the compound (Ib) or a salt thereof to deacylation reaction. Suitable method of this reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process 4

The compound (Id) or a salt thereof can be prepared by subjecting the compound (Ic) or a salt thereof to reduction reaction. This reduction reaction can be referred to that of the aforementioned Process 3.

Process 5

The compound (If) or a salt thereof can be prepared by reacting the compound (Ie) or a salt thereof with the compound (IV) or a salt thereof and the compound (V).

The reaction is usually carried out in a conventional solvent such as alcohol, tetrahydrofuran, N,N-dimethylformamide, dichloromethane, acetic acid, or any other solvent which does not adversely influence the reaction.

The reaction temperature is not critical and the reaction is usually carried out under cooling to heating.

Process 6

The compound (Ig) or a salt thereof can be prepared by reacting the compound (Ie) or a salt thereof with the compound (VI).

The reaction is usually carried out in a conventional solvent such as alcohol, tetrahydrofuran, N,N-dimethylformamide, dichloromethane, or any other solvent which does not adversely influence the reaction.

The reaction temperature is not critical and the reaction is usually carried out under cooling to warming.

Process 7

The compound (Ii) or a salt thereof can be prepared by subjecting the compound (Ih) or a salt thereof to hydrolysis reaction. This hydrolysis reaction can be referred to that of the aforementioned Process 3.

Process 8

The compound (Ij) or a salt thereof can be prepared by reacting the compound (Ii) or a salt thereof with the compound (VII) or a salt thereof.

The reaction is usually carried out in a conventional solvent such as alcohol, tetrahydrofuran, N,N-dimethylformamide, dichloromethane, acetic acid or any other solvent which does not adversely influence the reaction.

The reaction temperature is not critical and the reaction is usually carried out under cooling to heating.

Process 9

The compound (Il) or a salt thereof can be prepared by subjecting the compound (Ik) or a salt thereof to elimination reaction of the carboxy protective group. This reaction can be carried out in a similar manner to that of aforementioned Process 3.

Process 10

The compound (Id) or a salt thereof can be prepared by subjecting the compound (Im) or a salt thereof to elimination reaction of the amino protective group. This reaction can be carried out in a similar manner to that of aforementioned Process 3.

Process 11

The compound (In) or a salt thereof can be prepared by subjecting the compound (Id) or a salt thereof to acylation reaction.

This reaction can be carried out in a similar manner to that of aforementioned Process 2.

The processes for preparing the starting compound (II) are explained in the following.

Process A-①

The compound (X) or a salt thereof can be prepared by reacting a compound (VIII) or a salt thereof with a compound (IX) or a salt thereof.

This reaction can be carried out in accordance with the method disclosed in the Preparation 3 described later or a similar manner thereto.

Process A-②

The compound (XII) or a salt thereof can be prepared by reacting a compound (X) or a salt thereof with a compound (XI).

This reaction can be carried out in the presence or absence of a conventional solvent.

The reaction temperature is not critical and the reaction is usually carried out at ambient temperature, under warming or under heating.

Process A-③

The compound (XIII) or a salt thereof can be prepared by subjecting a compound (XII) or a salt thereof to hydrolysis.

The hydrolysis can be carried out in the presence of a base, and suitable base may be the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.) or the like.

This reaction is usually carried out in a solvent such as water, alcohol (e.g., methanol, ethanol, etc.), benzene, N,N-dimethylformamide, tetrahydrofuran, diethyl ether or any other solvent which does not adversely affect the reaction.

The reaction temperature is not critical and the reaction is usually carried out under cooling to warming.

Process A-④

The compound (II) or a salt thereof can be prepared by reacting a compound (XIII) or a salt thereof with a compound (XIV).

This reaction is usually carried out in the presence of a base such as tri(lower)alkylamine (e.g., trimethylamine, triethylamine, diisopropylethylamine, etc.), di(lower)alkylaniline (e.g., dimethylaniline, etc.) or the like.

This reaction is usually carried out in a solvent such as benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

The object compound (I) and pharmaceutically acceptable salts thereof are CCK antagonists and therefore useful as therapeutical agents for emesis, pancreatitis, etc.

Further, it is expected that the object compound (I) and pharmaceutically acceptable salts thereof have gastrin antagonism and are useful as therapeutical and/or preventive agents for ulcers, excess gastric secretion, zollinger-Ellison Syndrome, etc.

In order to show the utility of the object compound (I), some pharmacological activities of the representative compound thereof are shown in the following. [I] Test compound (1) (3RS)-1-(2-Fluorophenyl)-3,4,6,7-tetrahydro-3-(2-indolylcarbonylamino)-4-oxopyrrolo[3,2,1-jk][1,4]-benzodiazepine (hereinafter referred to as test compound A)

(2) (3S)-1-(2-Fluorophenyl)-3,4,6,7,-tetrahydro-3-(2-indolylcarbonylamino)-4-oxopyrrolo[3,2,1-jk][1,4]-benzodiazepine (hereinafter referred to as test compound B)

[II] Test (A) CCK receptor antagonism in isolated fundic circular muscle from guinea pig stomach test method The strip of circular muscle suspended in 25 ml organ bath containing Krebs' bicarbonate solution (NaCl 118 mM, KCl 4.8 mM, $KH_2PO_4$ 1.2 mM, $MgSO_4$ 1.2 mM, $CaCl_2$ 2.5 mM, $NaHCO_3$ 25 mM, glucose 11 mM and bovine serum albumin 0.1%) maintained at 37° C. and gassed with 95% $O_2$ and 5% $CO_2$.

The strip was placed under an initial tension of 0.5 g and equilibrated for 60 minutes during which the bath volume was replaced every 15 minutes. Isometric contraction was measured using a force transducer. CCK-8 ($3.2\times10^{-7}$M) was added to the bathing solution and the contractile force was measured. After washing out CCK-8, test compound A ($1\times10^{-6}$M) was added. 5 minutes later, CCK-8 was added and the contractile force was measured. CCK antagonism was calculated by comparing the contractile force induced by CCK in the absence or presence of test compound A.

test result

Inhibition (%): 90.4

(B) Inhibition of binding of [$^{125}$I] CCK-8 to rat pancreatic CCK receptors by test compound B (CCK antagonism)

$IC_{50}$: $6.7\times10^{-10}$M (C) Inhibition of binding of [$^{125}$I] CCK-8 to guinea pig cerebral cortical CCK receptors by test compound B (CCK antagonism)

$IC_{50}$: $3.1\times10^{-8}$M (D) Inhibitory effect of test compound B on caerulein-induced pancreatitis in mice $ED_{50}$: 0.022 mg/kg (E) Effect of test compound B upon CCK-8-induced inhibition of gastric emptying in mice (CCK antagonism)

$ED_{50}$: 0.010 mg/kg

The object compound (I) or pharmaceutically acceptable salts thereof can usually be administered to mammals including human being in the form of a conventional pharmaceutical composition such as capsule, micro-capsule, tablet, granule, powder, troche, syrup, aerosol, inhalation, solution, injection, suspension, emulsion, suppository or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

(1) To a solution of boron trichloride (4.5 ml) in toluene (30 ml) was added a solution of 3,4-dihydro-2H-1,4-benzoxazine (5.4 g), benzonitrile (5.05 g) and toluene (19 ml) over a period of 1 hour at 0°–5° C., and aluminum chloride (5.85 g) was added thereto. The mixture was heated under reflux for 16 hours. The reaction mixture was cooled to 5° C., and water (7 ml) was added thereto. After the addition of 2N hydrochloric acid, the mixture was heated under reflux for 2.5 hours and then cooled to 10° C. The separated organic layer and the extract from the aqueous layer with ethyl acetate were combined and washed with aqueous sodium hydroxide and water. The organic layer was dried over magnesium sulfate and evaporated. The residue was chromatographed on silica gel with an eluent of a mixture of n-hexane and ethyl acetate (10:1) to give 5-benzoyl-3,4-dihydro-2H-1,4-benzoxazine (5.7 g).

IR (Nujol): 3300, 1615, 1595, 1570, 1500 $cm^{-1}$

NMR ($CDCl_3$, δ): 3.50–3.75 (2H, m), 4.20–4.45 (2H, m), 6.30–7.85 (8H, m), 8.35 (1H, br s),

The following compounds were obtained according to a similar manner to that of Preparation 1(1).

(2) 7-(2-Fluorobenzoyl)indoline

IR (Nujol): 3370, 1615, 1605, 1575, 1565, 1495 $cm^{-1}$.

NMR ($CDCl_3$, δ): 3.15 (2H, tri, J=8 Hz), 3.87 (2H, tri, J=8 Hz), 6.33–6.70 (1H, m), 7.0–7.73 (7H, m).

(3) (2RS)-7-(2-Fluorobenzoyl)-2-methylindoline mp: 64°–66° C.

IR (Nujol): 3360, 1630, 1570, 1480, 1460, 1444, 1343, 1290, 1243, 1215, 1017, 753 $cm^{-1}$.

NMR ($CDCl_3$, δ): 1.37 (3H, d, J=6.8 Hz), 2.68 (1H, dd, J=16 Hz, 7 Hz), 3.31 (1H, dd, J=16 Hz, 9 Hz), 4.0–4.6 (1H, m), 6.3–7.7 (8H, m).

Preparation 2

(1) To a solution of 5-benzoyl-3,4-dihydro-2H-1,4-benzoxazine (5.74 g), pyridine (1.9 g) and methylene chloride (100 ml) was dropwise added a solution of bromoacetyl bromide (5.82 g) in methylene chloride (5 ml) at room temperature. After the mixture was stirred for 1.0 hour at the same temperature, water (100 ml) was added thereto under stirring. The organic layer was separated, washed with water, dried over magnesium sulfate and evaporated. The residue was crystallized with a mixture of diisopropyl ether and ethyl acetate. The crystals were collected by filtration to give 4-bromoacetyl-5-benzoyl-3,4-dihydro-2H-1,4-benzoxazine (6.0 g).

IR (Nujol): 1675, 1663, 1580 $cm^{-1}$.

NMR (DMSO-$d_6$, δ): 3.70–4.25 (2H, m), 4.10 (2H, s), 4.30–4.65 (2H, m), 6.85–7.90 (8H, m).

The following compounds were obtained according to a similar manner to that of Preparation 2(1).

(2) 1-Bromoacetyl-7-(2-fluorobenzoyl)indoline.

IR (Nujol): 1660, 1655, 1602, 1582 cm$^{-1}$.

NMR (CDCl$_3$, δ): 3.20 (2H, tri, J=8 Hz), 3.75 (2H, s), 4.20 (2H, tri, J=8 Hz), 6.90–7.95 (7H, m).

(3) (2RS)-1-Bromoacetyl-7-(2-fluorobenzoyl)-2-methylindoline mp: 110°–112° C.

IR (Nujol): 1667, 1639, 1445, 1391, 1275, 1223, 985, 750 cm$^{-1}$.

NMR (CDCl$_3$, δ): 1.38 (3H, d, J=6.8 Hz), 2.69 (1H, d, J=16 Hz), 3.53 (1H, dd, J=16 Hz, 8 Hz), 3.71 (2H, s), 4.67 (1H, broad quintet, J=7 Hz), 6.9–8.0 (7H, m).

Preparation 3

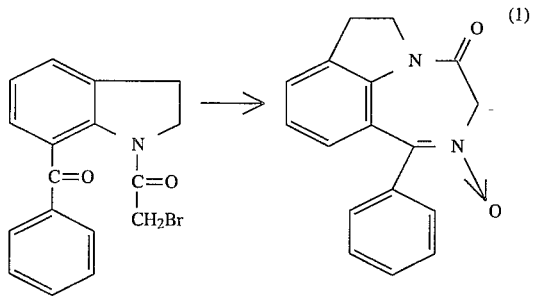

To a solution of sodium hydroxide (4.5 g), water (45 ml), hydroxyamine hydrochloride (8.95 g) and ethanol (45 ml) was added a mixture of 1-bromoacetyl-7-benzoylindoline (8.6 g) and ethanol (30 ml) over a period of 15 minutes at 50°–55° C. The mixture was stirred for 1.0 hour at the same temperature. Then, conc. hydrochloric acid (6 ml) was added to the reaction mixture. After stirring for 1.0 hour, the mixture was cooled in an ice-bath. The precipitates were collected by filtration, washed with ethanol and air-dried to give 3,4,6,7-tetrahydro-4-oxo-1-phenylpyrrolo[3,2,1-jk][1,4]benzodiazepine 2-oxide (5.25 g).

mp: 245°–250° C. (dec.).

IR (Nujol): 1663, 1590, 1515 cm$^{-1}$.

NMR (DMSO-d$_6$, δ): 3.16 (2H, tri, J=8 Hz), 4.18 (2H, tri, J=8 Hz), 4.63 (2H, s), 6.60–7.42 (8H, m).

MASS: m/e=278 (M$^+$).

The following compounds were obtained according to a similar manner to that of Preparation 3(1).

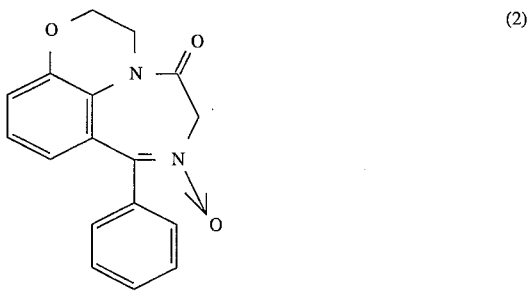

2,3,5,6-Tetrahydro-5-oxo-8-phenyl-1,4-oxazino[2,3,4-jk][1,4]benzodiazepine 7-oxide.

mp: 145°–150° C. (dec.).

IR (Nujol): 1665, 1580, 1530 cm$^{-1}$.

NMR (DMSO-d$_6$, δ): 2.90–3.50 (1H, m), 4.0–5.15 (5H, m), 6.45–7.75 (8H, m).

MASS: m/e=294 (M$^+$).

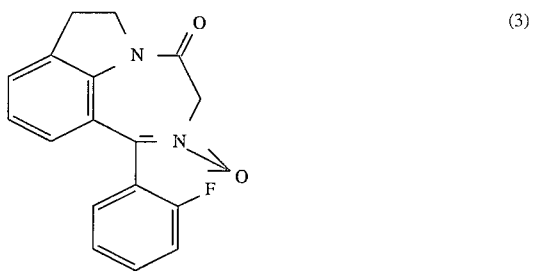

1-(2-Fluorophenyl)-3,4,6,7-tetrahydro-4-oxopyrrolo[3,2,1-jk][1,4]benzodiazepine 2-oxide.

IR (Nujol): 1675, 1665, 1608, 1585, 1570, 1512, 1488 cm$^{-1}$.

MASS: m/e=296 (M$^+$).

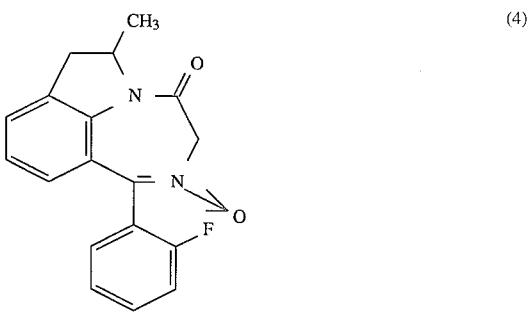

(6RS)-1-(2-Fluorophenyl)-3,4,6,7-tetrahydro-6-methyl-4-oxopyrrolo[3,2,1-jk][1,4]benzodiazepine 2-oxide.

mp: 184°–186° C. (dec.).

IR (Nujol): 1670, 1608, 1448, 1370, 1282, 1260, 1220, 1178, 1040, 760 cm$^{-1}$.

NMR (CDCl$_3$, δ): 1.40 (3H, d, J=6.4 Hz), 2.76 (1H, d, J=16 Hz), 3.58 (1H, dd, J=16, 7.8 Hz), 4.6–5.4 (3H, m/4.79, ABq, 2H), 6.8–7.6 (7H, m).

Preparation 4

(1) A mixture of 3,4,6,7-tetrahydro-4-oxo-1-phenylpyrrolo[3,2,1-jk][1,4]benzodiazepine 2-oxide (5.96 g) and acetic anhydride (42 ml) was stirred for 6.0 hours at room temperature. Then, to the cooled reaction mixture was added diisopropyl ether (120 ml). The precipitates were collected by filtration, washed with diisopropyl ether and air-dried to give (3RS)-3-acetoxy-3,4,6,7-tetrahydro-4-oxo-1-phenylpyrrolo[3,2,1-jk][1,4]benzodiazepine (6.24 g).

mp: 191°–193° C.

IR (Nujol): 1735, 1700, 1610, 1570 cm$^{-1}$.

NMR (DMSO-d$_6$, δ): 2.22 (3H, s), 3.0–3.40 (2H, m), 5.70 (1H, s), 3.70–4.10 (1H, m), 6.90–7.70 (8H, m), 4.20–4.60 (1H, m).

MASS: m/e=320 (M$^+$).

The following compounds were obtained according to a similar manner to that of Preparation 4(1).

(2) (6RS)-6-Acetoxy-2,3,5,6-tetrahydro-5-oxo-8-phenyl-1,4-oxazino[2,3,4-jk][1,4]benzodiazepine.

IR (Nujol): 1727, 1680, 1603, 1580, 1565 cm$^{-1}$.

NMR (DMSO-d$_6$, δ): 2.25 (3H, s), 3.10–3.50 (1H, m), 3.90–4.90 (3H, m), 6.03 (1H, s), 6.80–7.75 (8H, m).

(3) (3RS)-3-Acetoxy-1-(2-fluorophenyl)-3,4,6,7-tetrahydro-4-oxopyrrolo[3,2,1-jk][1,4]benzodiazepine.

IR (Nujol): 1746, 1690, 1600, 1581 cm$^{-1}$.

NMR (DMSO-d$_6$, δ): 2.20 (3H, s), 2.90–3.60 (2H, m), 3.73–4.20 (1H, m), 4.25–4.65 (1H, m), 5.80 (1H, s), 6.90–7.75 (7H, m).

Preparation 5

A solution of (6RS)-1-(2-fluorophenyl)-3,4,6,7-tetrahydro-6-methyl-4-oxopyrrolo[3,2,1-jk][1,4]-benzodiazepine 2-oxide (14.26 g) in acetic anhydride (100 ml) was heated at 80° C. under stirring for 45 minutes. The reaction mixture was cooled, and the resultant precipitate was collected by filtration and washed with diisopropyl ether to give a mixture (10.80 g) of (3RS,6RS)-3-acetoxy-1-(2-fluorophenyl)-3,4,6,7-tetrahydro-6-methyl-4-oxopyrrolo[3,2,1-jk][1,4]-benzodiazepine and (3RS,6SR)-3-acetoxy-1-(2-fluorophenyl)-3,4,6,7-tetrahydro-6-methyl-4-oxopyrrolo[3,2,1-jk][1,4]-benzodiazepine as light yellow crystal.

mp: 214°–216° C.

IR (Nujol): 1738, 1685, 1609, 1450, 1370, 1235, 1108, 1080, 793, 752 cm$^{-1}$.

NMR (CDCl$_3$, δ): 1.28 (3H, d, J=6 Hz), 2.32 (3H, s), 2.69 (1H, d, J=16.5 Hz), 3.50 (1H, dd, J=16.5 Hz, 9 Hz), 4.99 (1H, broad quintet, J=7.5 Hz), 5.90 (1H, s), 7.0–7.8 (7H, m).

Preparation 6

(1) To a mixture of (3RS)-3-acetoxy-3,4,6,7-tetrahydro-4-oxo-1-phenylpyrrolo[3,2,1-jk][1,4]benzodiazepine (3.95 g) and ethanol (123 ml) was added 1N aqueous sodium hydroxide (12.3 ml) at room temperature. After stirring for 15 minutes, water (100 ml) was added to the reaction mixture, and the mixture was adjusted to pH 4.0 with 6N hydrochloric acid. The ethanol was evaporated, and the resultant precipitates were collected by filtration and dried over phosphorus pentoxide to give (3RS)-3,4,6,7-tetrahydro-3-hydroxy-4-oxo-1-phenylpyrrolo[3,2,1-jk][1,4]benzodiazepine (3.36 g).

IR (Nujol): 3160, 1690, 1600, 1580, 1563 cm$^{-1}$.

NMR (DMSO-d$_6$, δ): 3.0–3.50 (2H, m), 3.60–4.10 (1H, m), 4.20–4.60 (1H, m), 4.70 (1H, d, J=8 Hz), 6.26 (1H, d, J=8 Hz), 6.95–7.60 (8H, m).

The following compounds were obtained according to a similar manner to that of Preparation 6(1).

(2) (6RS)-2,3,5,6-Tetrahydro-6-hydroxy-5-oxo-8-phenyl-1,4-oxazino[2,3,4-jk][1,4]benzodiazepine mp: 205°–210° C. (dec.).

IR (Nujol): 1680, 1600, 1580, 1565 cm$^{-1}$.

NMR (DMSO-d$_6$, δ): 2.90–3.50 (1H, m), 4.0–5.0 (3H, m), 5.0 (1H, d, J=9 Hz), 6.40 (1H, d, J=9 Hz), 6.75–7.70 (8H, m).

MASS: m/e=294 (M$^+$).

(3) (3RS)-1-(2-Fluorophenyl)-3,4,6,7-tetrahydro-3-hydroxy-4-oxopyrrolo[3,2,1-jk][1,4]benzodiazepine.

IR (Nujol): 3425, 1665, 1609, 1595, 1582 cm$^{-1}$.

NMR (DMSO-d$_6$, δ): 3.03–3.50 (2H, m), 3.60–4.25 (1H, m), 4.25–4.70 (1H, m), 4.78 (1H, d, J=8 Hz), 6.40 (1H, d, J=8 Hz), 7.0–7.90 (7H, m).

(4) Mixture of (3RS,6RS)-1-(2-fluorophenyl)-3,4,6,7-tetrahydro-3-hydroxy-6-methyl-4-oxopyrrolo[3,2,1-jk]-[1,4]benzodiazepine and (3RS,6SR)-1-(2-fluorophenyl)-3,4,6,7-tetrahydro-3-hydroxy-6-methyl-4-oxopyrrolo-[3,2,1-jk][1,4]benzodiazepine.

mp: 186°–187° C.

IR (Nujol): 3400, 1660, 1610, 1450, 1385, 1345, 1296, 1250, 1142, 762, 750 cm$^{-1}$.

NMR (CDCl$_3$, δ): 1.31 (3H, d, J=6 Hz), 2.72 (1H, d, J=16.5 Hz), 3.51 (1H, dd, J=16.5 Hz, 9 Hz), 4.7–5.2 (3H, m,/4.85, s), 6.8–7.7 (7H, m).

Example 1

(1) To a solution of (3RS)-3,4,6,7-tetrahydro-3-hydroxy-4-oxo-1-phenylpyrrolo[3,2,1-jk][1,4]benzodiazepine (1.4 g) in tetrahydrofuran (40 ml) were added diisopropylethylamine (0.97 g) and mesyl chloride (0.86 g) at 5° C. Then, after the mixture was stirred for 2.0 hours at room temperature, 9N ammonia in methanol (30 ml) was added to the cooled reaction mixture. The reaction mixture was stirred for 1.5 hours at room temperature. After solvent was evaporated, the residue was mixed with a mixture of water and ethyl acetate under stirring. Then, the separated organic layer was dried over magnesium sulfate and evaporated. The residue was chromatographed on silica gel with an eluent of a mixture of chloroform and methanol (15:1) to give (3RS)-3-amino-3,4,6,7-tetrahydro-4-oxo-1-phenylpyrrolo[3,2,1-jk][1,4]-benzodiazepine (460 mg).

NMR (CDCl$_3$, δ): 2.40 (2H, br s), 2.90–3.60 (2H, m), 3.73–4.15 (1H, m), 4.35 (1H, s), 4.50–4.85 (1H, m), 6.93–7.65 (8H, m).

The following compounds were obtained according to a similar manner to that of Example 1(1).

(2) (6RS)-6-Amino-2,3,5,6-tetrahydro-5-oxo-8-phenyl-1,4-oxazino[2,3,4-jk][1,4]benzodiazepine.

NMR (CDCl$_3$, δ): 2.85–3.50 (1H, m), 3.90–5.20 (6H, m), 6.80–8.0 (8H, m).

(3) (3RS)-3-Amino-1-(2-fluorophenyl)-3,4,6,7-tetrahydro-4-oxopyrrolo[3,2,1-jk][1,4]benzodiazepine.

NMR (CDCl$_3$, δ): 2.63 (2H, br s), 3.03–3.50. (2H, m), 3.63–4.35 (1H, m), 4.35–4.95 (1H, m), 4.45 (1H, s), 6.85–7.80 (7H, m).

(4) Mixture of (3RS,6RS)-3-amino-1-(2-fluorophenyl)-3,4,6,7-tetrahydro-6-methyl-4-oxopyrrolo[3,2,1-jk][1,4]-benzodiazepine and (3RS,6SR)-3-amino-1-(2-fluorophenyl)-3,4,6,7-tetrahydro-6-methyl-4-oxopyrrolo[3,2,1-jk][1,4]-benzodiazepine.

IR (Neat): 3350, 1688, 1610, 1445, 1220, 1042, 750 cm$^{-1}$.

NMR (CDCl$_3$, δ): 1.27 & 1.73 (total 3H, each d, J=6 Hz), 2.59 (2H, s), 2.5–3.6 (2H, m), 4.30 & 4.47 (total 1H, each s), 4.5–5.2 (1H, m), 6.8–7.7 (7H, m).

Example 2

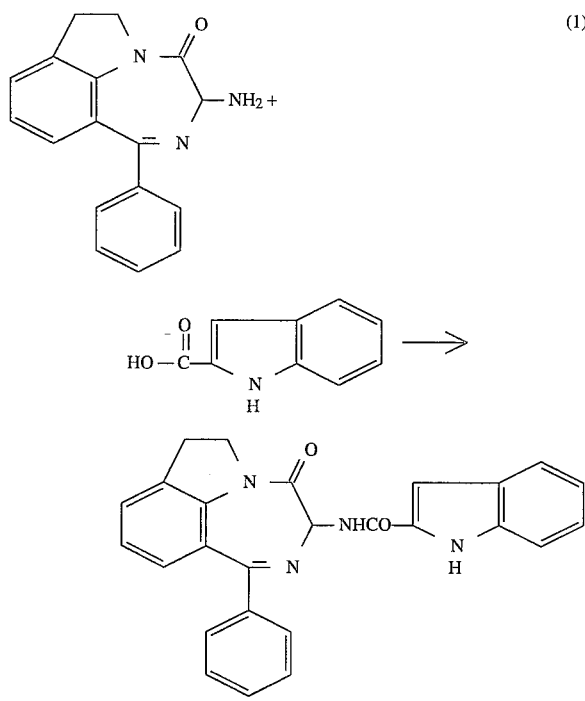

A mixture of (3RS)-3-amino-3,4,6,7-tetrahydro-4-oxo-1-phenylpyrrolo[3,2,1-jk][1,4]benzodiazepine (430 mg), indole-2-carboxylic acid (250 mg), 1-hydroxybenzotriazole (210 mg) and N,N-dimethylformamide (5 ml) was stirred at 5° C., and N-ethyl-N'-(3-dimethylaminopropyl)carbodiimide hydrochloride (298 mg) and triethylamine (160 mg) were added thereto. The mixture was stirred for 1.0 hour at room temperature. Then, the reaction mixture was poured into a mixture of ethyl acetate and water. The organic layer was separated, washed with water, dried over magnesium sulfate and evaporated. The residue was chromatographed on silica gel with an eluent of a mixture of chloroform and ethyl acetate (10:1) to give (3RS) -3,4,6,7-tetrahydro-3-(2-indolylcarbonylamino)-4-oxo-1-phenylpyrrolo[3,2,1-jk][1,4]benzodiazepine (0.405 g).

mp: 180°–185° C. (dec.)

NMR (CDCl$_3$, δ): 2.90–3.50 (2H, m), 3.75–4.20 (1H, m), 4.50–4.85 (1H, m), 5.65 (1H, d, J=8 Hz), 6.90–7.70 (13H, m), 8.03 (1H, d, J=8 Hz), 9.85 (1H, br s),

MASS: m/e=420 (M$^+$).

The following compounds were obtained according to a similar manner to that of Example 2(1).

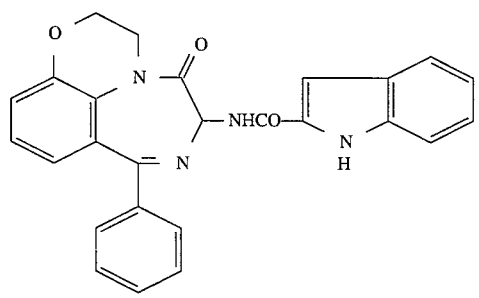

(6RS)-2,3,5,6-Tetrahydro-6-(2-indolylcarbonylamino)-5-oxo-8-phenyl-1,4-oxazino[2,3,4-jk][1,4]benzodiazepine.

mp: 180°–185° C. (dec.).

NMR (DMSO-d$_6$, δ): 3.10–3.50 (1H, m), 4.0–4.90 (3H, m), 5.76 (1H, d, J=8 Hz), 6.80–7.75 (13H, m), 9.45 (1H, d, J=8 Hz).

MASS: m/e=436 (M$^+$),

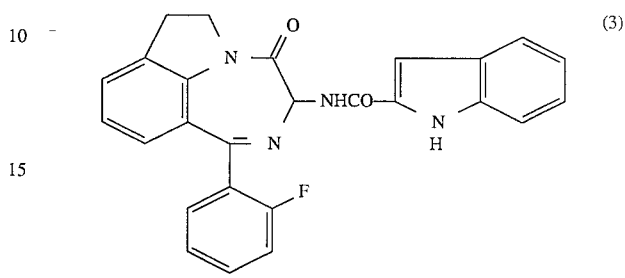

(3RS)-1-(2-Fluorophenyl)-3,4,6,7-tetrahydro-3-(2-indolylcarbonylamino)-4-oxopyrrolo[3,2,1-jk][1,4]-benzodiazepine mp: 280°–285° C. (dec.)

IR (Nujol): 3390, 3250, 1678, 1640, 1610, 1600, 1580, 1531, 1500, 1482 cm$^{-1}$.

NMR (DMSO-d$_6$, δ): 3.10–3.65 (2H, m), 3.70–4.20 (1H, m), 4.30–4.70 (1H, m), 5.57 (1H, d, J=8 Hz), 6.90–7.75 (12H, m), 9.53 (1H, d, J=8 Hz).

MASS: m/e=438 (M$^+$).

(4) Mixture of (3RS,6RS)-1-(2-fluorophenyl)-3,4,6,7-tetrahydro-3-(2-indolylcarbonylamino)-6-methyl-4-oxo-pyrrolo[3,2,1-jk][1,4]benzodiazepine and (3RS,6SR)-1-(2-fluoropheynyl)-3,4,6,7-tetrahydro-3-(2-indolylcarbonylamino)-6-methyl-4-oxopyrrolo[3,2,1-jk][1,4]benzodiazepine.

mp: >250° C.

IR (Nujol): 3400, 3270, 1675, 1638, 1610, 1532, 1450, 1373, 1340, 1225, 1118, 770, 755, 738 cm$^{-1}$.

NMR (DMSO-d$_6$, δ): 1.11 & 1.54 (total 3H, each d, J=6 Hz), 2.5–3.8 (2H, m), 4.5–5.1 (1H, m), 5.43 & 5.47 (total 1H, each d, J=8 Hz), 6.9–7.7 (7H, m), 9.43 (1H, d, J=8 Hz), 11.6 (1H, br s).

MASS: m/e=452 (M$^+$).

Preparation 7

The following compound was obtained according to a similar manner to that of Preparation 1(1).

8-(2-Fluorobenzoyl)-1,2,3,4-tetrahydroquinoline.

IR (Nujol): 3300, 3060, 1615, 1609, 1580, 1510, 1490 cm$^{-1}$.

NMR (CDCl$_3$, δ): 1.70–2.10 (2H, m), 2.65–2.95 (2H, m), 3.35–3.65 (2H, m), 6.20–6.48 (1H, m), 6.95–7.75 (6H, m), 9.05 (1H, br s).

Preparation 8

The following compound was obtained according to a similar manner to that of Preparation 2(1).

1-Bromoacetyl-8-(2-fluorobenzoyl)-1,2,3,4-tetrahydroquinoline.

NMR (CDCl$_3$, δ): 1.45–4.45 (8H, m), 6.90–7.95 (7H, m).

Preparation 9

The following compound was obtained according to a similar manner to that of Preparation 3(1).

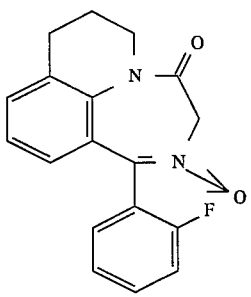

1-(2-Fluorophenyl)-3,4,7,8-tetrahydro-4-oxo-6H-pyrido[3,2,1-jk][1,4]benzodiazepine 2-oxide.

NMR (DMSO-$d_6$, δ): 1.65–2.35 (2H, m), 2.70–3.50 (3H, m), 4.25–4.80 (1H, m), 4.48, 4.88 (2H, ABq, J=12 Hz), 6.75–7.70 (7H, m)

Preparation 10

The following compound was obtained according to a similar manner to that of Preparation 4(1).

(3RS)-3-Acetoxy-1-(2-fluorophenyl)-3,4,7,8-tetrahydro-4-oxo-6H-pyrido[3,2,1-jk][1,4]benzodiazepine.

NMR (DMSO-$d_6$, δ): 1.65–2.40 (2H, m), 2.23 (3H, s), 2.75–3.85 (3H, m), 4.15–4.70 (1H, m), 5.80 (1H, s), 6.95–7.85 (7H, m).

Preparation 11

The following compound was obtained according to a similar manner to that of Preparation 6(1).

(3RS)-1-(2-Fluorophenyl)-3,4,7,8-tetrahydro-3-hydroxy-4-oxo-6H-pyrido[3,2,1-jk][1,4]benzodiazepine.

NMR (DMSO-$d_6$, δ): 1.63–2.40 (2H, m), 2.75–3.50 (3H, m), 4.0–4.75 (1H, m), 4.83 (1H, d, J=9 Hz), 6.35 (1H, d, J=9 Hz), 6.90–7.90 (7H, m).

MASS: m/e=310 ($M^+$).

Example 3

The following compound was obtained according to a similar manner to that of Example 1(1).

(3RS)-3-Amino-1-(2-Fluorophenyl)-3,4,7,8-tetrahydro-4-oxo-6H-pyrido[3,2,1-jk][1,4]benzodiazepine.

NMR (CDCl$_3$, δ): 1.60–2.50 (2H, m), 2.6–3.55 (3H, m), 3.08 (2H, s), 4.25–4.85 (1H, m), 4.55 (1H, s), 6.80–7.85 (7H, m).

Example 4

(1) To a solution of (3RS)-3-amino-3,4,6,7-tetrahydro-4-oxo-1-phenylpyrrolo[3,2,1-jk][1,4]benzodiazepine (28.54 g) in N,N-dimethylformamide (285 ml) were added N-tert-butoxycarbonyl-L-phenylalanine (27.33 g), 1-hydroxybenzotriazole (13.92 g) and N,N'-dicyclohexylcarbodiimide (21.25 g) under stirring at ambient temperature. The mixture was stirred for two hours under the same conditions and the resultant precipitates were filtered off. The filtrate and the washings (ethyl acetate) were combined and poured into a mixture of ethyl acetate (500 ml) and water (500 ml) under stirring. The separated organic layer was washed with water, aqueous sodium bicarbonate and water. After being dried over magnesium sulfate, the organic solvent was removed under reduced pressure. The residue was chromatographed on silica gel with an eluent of a mixture of chloroform and ethyl acetate (10:1) to give a mixture (48.82 g) of (3R)-3-[((2S)-2-tert-butoxycarbonylamino-3-phenylpropanoyl)amino]-3,4,6,7-tetrahydro-4-oxo-1-phenylpyrrolo[3,2,1-jk][1,4]benzodiazepine and (3S)-3-[((2S)-2-tert-butoxycarbonylamino-3-phenylpropanoyl)amino]-3,4,6,7-tetrahydro-4-oxo-1-phenylpyrrolo[3,2,1-jk][1,4]benzodiazepine as amorphous substance.

NMR (CDCl$_3$, δ): 1.41 and 1.43 (9H, each s), 2.9–3.5 (4H, m), 3.8–4.0 (1H, m), 4.6–4.7 (2H, m), 5.0–5.1 (1H, broad s), 5.4 (1H, d, J=8 Hz), 7.0–7.8 (14H, m).

The following compound was obtained according to a similar manner to that of Example 4(1).

(2) Mixture of (3R)-3-[((2S)-2-tert-butoxycarbonylamino-3-phenylpropanoyl)amino]-1-(2-fluorophenyl)-3,4,6,7-tetrahydro-4-oxopyrrolo[3,2,1-jk][1,4]benzodiazepine and (3S)-3-[((2S)-2-tert-butoxycarbonylamino-3-phenylpropanoyl)amino]-1-(2-fluorophenyl)-3,4,6,7-tetrahydro-4-oxopyrrolo[3,2,1-jk][1,4]benzodiazepine.

NMR (CDCl$_3$, δ): 1.40 (9H, s), 2.93–5.20 (9H, m), 6.85–7.90 (13H, m).

Example 5

Hydrogen chloride was bubbled into a solution of a mixture (48.50 g) of (3R)-3-[((2S)-2-tert-butoxy-carbonylamino-3-phenylpropanoyl)amino]-3,4,6,7-tetrahydro-4-oxo-1-phenylpyrrolo[3,2,1-jk][1,4]benzodiazepine and (3S)-3-[((2S)-2-tert-butoxycarbonylamino-3-phenylpropanoyl)amino]-3,4,6,7-tetrahydro-4-oxo-1-phenylpyrrolo[3,2,1-jk][1,4]benzodiazepine in ethyl acetate (1.0 l) under cooling in an ice-bath and stirring. After the mixture was saturated with hydrogen chloride, the resultant mixture was stirred at ambient temperature for one hour. Hydrogen chloride was removed by bubbling nitrogen. To the resultant mixture was added water and the mixture was stirred well. The aqueous layer was separated and the organic layer was washed with water. The separated aqueous layer and washings were combined, neutralized with 20% aqueous sodium hydroxide and extracted with ethyl acetate twice. After the extracts were dried over magnesium sulfate, the solvent was evaporated under reduced pressure to give solid. The solid was collected by filtration and washed with a small amount of ethyl acetate and ethyl ether in turn to give crude compound (13.42 g), which was recrystallized from ethanol to afford (3R)-3-[((2S)-2-amino-3-phenylpropanoyl)amino]-3,4,6,7-tetrahydro-4-oxo-1-phenylpyrrolo[3,2,1-jk][1,4]benzodiazepine (11.33 g) as light pink fine needles.

mp: 94°–95° C.

IR (Nujol): 3350, 3150, 1672, 1644, 1597, 1550, 1445, 1372, 1237, 734, 699 cm$^{-1}$.

NMR (CDCl$_3$, δ): 1.62 (2H, broad s), 2.74 (1H, dd, J=14.0, 10.5 Hz), 3.1–3.5 (3H, m), 3.75 (1H, dd, J=3.5, 10.5 Hz), 3.92 (1H, q, J=10.5 Hz), 4.66 (1H, t, J=10.5 Hz), 5.45 (1H, d, J=8.4 Hz), 7.06–7.6 (13H, m), 8.94 (1H, d, J=8.4 Hz).

Mass: m/e=424 ($M^+$).

On the other hand, the filtrate was evaporated under reduced pressure. After the residue was triturated with a small amount of ethyl acetate, the precipitate was collected by filtration. Recrystallization from ethanol (two times) gave (3S)-3-[((2S)-2-amino-3-phenylpropanoyl)amino]-3,4,6,7-tetrahydro-4-oxo-1-phenylpyrrolo[3,2,1-jk][1,4]benzodiazepine (9.70 g) as colorless needles.

mp: 203°–204° C.

IR (Nujol): 3340, 3250, 1680 (sh), 1674, 1660, 1596, 1485, 1445, 1393, 1328, 890, 756, 732, 702 cm$^{-1}$.

NMR (CDCl$_3$, δ): 1.47 (2H, broad s), 2.85 (1H, dd, J=14.0, 10.5 Hz), 3.1–3.5 (3H, m), 3.75 (1H, dd, J=3.5, 10.5 Hz), 3.97 (1H, q, J=10.5 Hz), 4.64 (1H, t, J=10.5 Hz), 5.47 (1H, d, J=8.4 Hz), 7.1–7.6 (13H, m), 8.95 (1H, d, J=8.4 Hz).

MASS: m/e=424 (M$^+$).

Example 6

The following compounds were obtained according to a similar manner to that of Example 5.

(3R)-3-[((2S)-2-Amino-3-phenylpropanoyl)amino]-1-(2-fluorophenyl)-3,4,6,7-tetrahydro-4-oxopyrrolo[3,2,1-jk][1,4]benzodiazepine.

NMR (CDCl$_3$, δ): 1.63 (2H, s), 2.60–4.90 (8H, m), 5.48 (1H, d, J=8 Hz), 6.80–7.85 (12H, m), 9.0 (1H, d, J=8 Hz).

(3S)-3-[((2S)-2-Amino-3-phenylpropanoyl)amino]-1-(2-fluorophenyl)-3,4,6,7-tetrahydro-4-oxopyrrolo[3,2,1-jk][1,4]benzodiazepine.

NMR (CDCl$_3$, δ): 1.65 (2H, s), 2.60–4.90 (8H, m), 5.50 (1H, d, J=8 Hz), 6.80–7.90 (12H, m), 8.95 (1H, d, J=8 Hz).

Example 7

To a solution of (3S)-3-[((2S)-2-amino-3-phenylpropanoyl)amino]-3,4,6,7-tetrahydro-4-oxo-1-phenylpyrrolo[3,2,1-jk][1,4]benzodiazepine (2.91 g) in methylene chloride (60 ml) was added phenylisothiocyanate (1.08 g) and the mixture was heated to remove methylene chloride and the resultant residue was completely evaporated under reduced pressure. The viscous residue was chromatographed on silica gel. The elution was carried out with chloroform and a mixture of chloroform and methanol (50:1) to afford (3S)-3,4,6,7-tetrahydro-1-phenyl-3-[[(2S)-2-{N'-(phenyl)thioureido}-3-phenylpropanoyl]amino]-4-oxopyrrolo[3,2,1-jk][1,4]benzodiazepine (2.95 g) as an amorphous substance.

Example 8

A solution of (3S)-3,4,6,7-tetrahydro-1-phenyl-3-[[(2S)-2-{N'-(phenyl)thioureido}-3-phenylpropanoyl]amino]-4-oxopyrrolo[3,2,1-jk][1,4]benzodiazepine (2.90 g) in trifluoroacetic acid (10 ml) was stirred for 0.5 hours at 50° C. The reaction mixture was evaporated under reduced pressure to dryness and the residue was chromatographed on silica gel with a mixture of chloroform and methanol (15:1) as an eluent. The fractions containing the desired product were combined and washed with diluted aqueous sodium bicarbonate. The organic layer was separated, dried over magnesium sulfate and evaporated to give (3S)-3-amino-3,4,6,7-tetrahydro-4-oxo-1-phenylpyrrolo-[3,2,1-jk][1,4] benzodiazepine (0.97 g) as an amorphous substance.

NMR (CDCl$_3$, δ): 2.38 (2H, br s), 3.0–3.5 (2H, m), 3.8–4.15 (1H, m), 4.38 (1H, s), 4.5–4.8 (1H, m), 6.95–7.65 (8H, m).

$[\alpha]_D^{20}$=−175.09° (c=0.518, CHCl$_3$).

Example 9

(1) To a solution of (3R)-3-[((2S)-2-amino-3-phenylpropanoyl)amino]-3,4,6,7-tetrahydro-4-oxo-1-phenylpyrrolo[3,2,1-jk][1,4]benzodiazepine (1.99 g) in methylene chloride (30 ml) was added phenylisothiocyanate (0.76 g) and the mixture was heated to remove methylene chloride and the resultant residue was completely evaporated under reduced pressure. The residue was dissolved in trifluoroacetic acid (7 ml) and the mixture was stirred at 50° C. for 25 minutes. Removal of trifluoroacetic acid gave viscous oil, which was chromatographed on silica gel with a mixture of chloroform and methanol (15:1) as an eluent. The fractions containing the desired product were combined and washed with diluted aqueous sodium bicarbonate. The organic layer was separated and dried over magnesium sulfate. Removal of the solvent gave (3R)-3-amino-3,4,6,7-tetrahydro-4-oxo-1-phenylpyrrolo[3,2,1-jk][1,4]-benzodiazepine (0.91 g) as an amorphous substance.

NMR (CDCl$_3$, δ): 2.40 (2H, br s), 3.0–3.5 (2H, m), 3.8–4.3 (1H, m), 4.40 (1H, br s), 4.5–4.8 1H, m), 7.0–7.8 (8H, m).

$[\alpha]_D^{20}$=146.44° (c=0.574, CHCl$_3$).

The following compounds were obtained according to a similar manner to that of Example 9(1).

(2) (3S)-3-Amino-1-(2-fluorophenyl)-3,4,6,7-tetrahydro-4-oxopyrrolo[3,2,1-jk][1,4]benzodiazepine.

$[\alpha]_D^{25}$=−73.4° (c=0.475, CHCl$_3$).

(3) (3R)-3-Amino-1-(2-fluorophenyl)-3,4,6,7-tetrahydro-4-oxopyrrolo[3,2,1-jk][1,4]benzodiazepine.

$[\alpha]_D^{25}$=67° (c=0.432, CHCl$_3$).

Example 10

(1) To a solution of 2-amino-4-chlorobenzoic acid (418.7 mg) and N-methylmorpholine (246.8 mg) in a mixture of methylene chloride and N,N-dimethylformamide (10:1, 35 ml) was dropwise added isobutyl chloroformate (333.3 mg) under cooling at −10° C. in an ice-salt bath and stirring. The mixture was stirred at the same temperature for 15 minutes and warmed to 0° C. To the resultant mixture was dropwise added a solution of (3RS)-3-amino-3,4,6,7-tetrahydro-4-oxo-1-phenylpyrrolo[3,2,1-jk][1,4]benzodiazepine (554.7 mg) in a mixture of methylene chloride and N,N-dimethylformamide (10:1, 5 ml) under the same conditions. The mixture was stirred for one hour at the same temperature and 12 hours at ambient temperature. Methylene chloride was removed from the reaction mixture. Ethyl acetate and an aqueous solution of sodium bicarbonate were added to the mixture under stirring. The separated organic layer was washed with water twice and dried over magnesium sulfate. Removal of the solvent under reduced pressure afforded a brown oil (1.22 g), which was chromatographed on silica gel with an eluent of chloroform. The fractions containing the desired compound were combined and evaporated to give an amorphous substance, which was powdered by stirring in diisopropyl ether overnight. The white powder was collected by filtration and washed with diisopropyl ether to give (3RS)-3-[(2-amino-4-chlorobenzoyl)amino]-3,4,6,7-tetrahydro-4-oxo-1-phenylpyrrolo[3,2,1-jk][1,4]benzodiazepine (213.5 mg).

mp: 145°–148° C. (dec.).

IR (Nujol): 3410, 3320, 1685 (sh), 1675, 1640, 1610, 1505, 1447, 1373, 1240, 1165, 918, 860, 832, 695 cm$^{-1}$.

NMR (CDCl$_3$, δ): 3.0–3.4 (2H, m), 3.7–4.1 (1H, m), 4.4–4.8 (1H, m), 5.58 (1H, d, J=8 Hz), 5.68 (2H, br s), 6.6–7.6 (11H, m), 7.86 (1H, d, J=8 Hz).

MASS: m/e=430 (M$^+$).

The following compounds were obtained according to a similar manner to that of Example 10(1).

(2) (3RS)-3-[(2-Amino-4-chlorobenzoyl)amino]-1-(2-fluorophenyl)-3,4,6,7-tetrahydro-4-oxopyrrolo[3,2,1-jk]-[1,4]benzodiazepine.

mp: 200°–205° C.

IR (Nujol): 3420, 3300, 1675, 1640, 1570, 1500, 1255, 915, 755 cm$^{-1}$.

NMR (DMSO-d$_6$, δ): 2.83–3.6 (2H, m), 3.6–4.7 (1H, m), 4.2–4.67 (1H, m), 5.35 (1H, d, J=8 Hz), 6.33–7.63 (11H, m), 7.72 (1H, d, J=9 Hz), 6.22 (1H, d, J=8 Hz).

MASS: m/e=447 (M$^+$).

(3) 3-((E)-Cinnamoylamino)-1-(2-fluorophenyl)-3,4,6,7-tetrahydro-4-oxopyrrolo[3,2,1-jk][1,4]-benzodiazepine.

mp: 189°–190° C.

IR (Nujol): 3290, 1675, 1650, 1620, 1530 cm$^{-1}$.

NMR (CDCl$_3$, δ): 3.0–3.6 (2H, m), 3.8–4.8 (1H, m), 5.55 (1H, d, J=8 Hz), 6.58 (1H, d, J=15 Hz), 6.83–7.8 (15H, m).

MASS: m/e=425 (M$^+$), 294 (M$^+$-131).

(4) (3RS)-1-(2-Fluorophenyl)-3,4,6,7-tetrahydro-4-oxo-3-[(4-trifluoromethylbenzoyl)amino]pyrrolo[3,2,1-jk][1,4]-benzodiazepine.

mp: 199°–201° C.

IR (Nujol): 3300, 1670, 1640, 1530, 1325, 1120, 1065, 850 cm$^{-1}$.

NMR (CDCl$_3$, δ): 2.87–3.4 (2H, m), 3.8–4.23 (1H, m), 4.43–4.8 (1H, m), 5.55 (1H, d, J=8 Hz), 6.8–8.13 (12H, m).

MASS: m/e=467 (M$^+$).

(5) (3RS)-3,4,6,7-Tetrahydro-1-phenyl-3-[(4-trifluoromethylbenzoyl)amino]-4-oxopyrrolo[3,2,1-jk][1,4]-benzodiazepine.

mp: 232°–235° C.

IR (Nujol): 3350, 3230, 1690, 1660, 1545, 1320, 1240, 1170, 1125, 1060, 860 cm$^{-1}$.

NMR (CDCl$_3$, δ): 3.07–3.49 (2H, m), 3.92–4.08 (1H, m), 4.62–4.74 (1H, m), 5.62 (1H, d, J=8 Hz), 7.10–8.11 (13H, m).

MASS: m/e=449 (M$^+$).

(6) (3RS)-3-((E)-Cinnamoylamino)-3,4,6,7tetrahydro-1-phenyl-4-oxopyrrolo[3,2,1-jk][1,4]-benzodiazepine.

mp: 224°–226° C.

IR (Nujol): 3300, 1680, 1655, 1625, 1510, 1210 cm$^{-1}$.

NMR (CDCl$_3$, δ): 2.77–3.5 (2H, m), 3.67–4.1 (1H, m), 4.4–4.77 (1H, m), 5.48 (1H, d, J=8 Hz), 6.43–7.77 (16H, m).

MASS: m/e=407 (M$^+$).

Example 11

(1) To a solution of (3RS)-3-amino-3,4,6,7-tetrahydro-4-oxo-1-phenylpyrrolo[3,2,1-jk][1,4]benzodiazepine (0.56 g) in dry tetrahydrofuran (8 ml) was added 4-chlorophenyl isocyanate (0.31 g) under stirring at ambient temperature. To the mixture was added an additional tetrahydrofuran (4 ml). The mixture was stirred for 4 hours at ambient temperature. The white precipitates were collected by filtration, washed with cold tetrahydrofuran and diethyl ether successively and dried to afford (3RS)-3-[N'-(4-chlorophenyl)ureido]-3,4,6,7-tetrahydro-4-oxo-1-phenylpyrrolo[3,2,1-jk][1,4]benzodiazepine (0.48 g) as a white powder.

mp: 263°–265° C. (dec.).

IR (Nujol): 3350, 3250, 1680 (sh), 1672, 1645, 1600, 1547, 1487, 1444, 1396, 1388, 1302, 1217, 1166, 825, 695 cm$^{-1}$.

NMR (DMSO-d$_6$, δ): 3.1–3.6 (2H, m), 3.7–4.3 (1H, m), 4.3–4.7 (1H, m), 5.18 (1H, d, J=8 Hz), 7.2–7.8 (13H, m), 9.27 (1H, broad s)

MASS: m/e=430 (M$^+$).

The following compounds were obtained according to a similar manner to that of Example 11(1).

(2) (3RS)-3-[N'-(4-Chlorophenyl)ureido]-1-(2-fluorophenyl)-3,4,6,7-tetrahydro-4-oxopyrrolo[3,2,1-jk]-[1,4]benzodiazepine.

mp: 262°–264° C. (dec.).

IR (Nujol): 3250, 1675, 1640, 1600, 1545, 1490, 1300, 1215, 820, 750 cm$^{-1}$.

NMR (DMSO-d$_6$, δ): 2.93–3.5 (2H, m), 3.67–4.1 (1H, m), 4.23–4.6 (1H, m), 5.08 (1H, d, J=8 Hz), 6.9–7.67 (12H, m), 9.1 (1H, br s).

(3) (3RS)-3-[N'-(2-Chlorophenyl)ureido]-3,4,6,7-tetrahydro-4-oxo-1-phenylpyrrolo[3,2,1-jk][1,4]-benzodiazepine.

mp: 258°–260° C. (dec.).

IR (Nujol): 3250, 1680, 1640, 1580, 1550 cm$^{-1}$.

NMR (DMSO-d$_6$, δ): 2.87–3.5 (2H, m), 3.7–4.1 (1H, m), 4.2–4.63 (1H, m), 5.13 (1H, d, J=8 Hz), 6.8–7.7 (11H, m), 8.07 (1H, d, J=8 Hz), 8.43 (1H, d, J=9 Hz), 8.63 (1H, br s).

(4) (3RS)-3-[N'-(2-Chlorophenyl)ureido]-1-(2-fluorophenyl)-3,4,6,7-tetrahydro-4-oxopyrrolo[3,2,1-jk]-[1,4]benzodiazepine.

mp: 240°–241° C.

IR (Nujol): 3270, 1670, 1640, 1590, 1535 cm$^{-1}$.

NMR (DMSO-d$_6$, δ): 3.0–3.5 (2H, m), 3.83–4.67 (1H, m), 5.17 (1H, d, J=8 Hz), 6.9–7.63 (10H, m), 8.08 (1H, d, J=9 Hz), 8.45 (1H, d, J=8 Hz), 8.63 (1H, s).

(5) (3RS)-1-(2-Fluorophenyl)-3,4,6,7-tetrahydro-3-[N'-(3-methoxyphenyl)ureido]-4-oxopyrrolo-[3,2,1-jk][1,4]benzodiazepine.

mp: 242°–243° C.

IR (Nujol): 3280, 1670, 1630, 1605, 1550, 1285, 1210, 1155 cm$^{-1}$.

NMR (DMSO-d$_6$, δ): 2.9–3.5 (2H, m), 3.67 (3H, s), 3.8–4.7 (2H, m), 5.13 (1H, d, J=8 Hz), 6.4–7.7 (12H, m), 9.0 (1H, br s).

MASS: m/e=444 (M$^+$).

(6) (3RS)-3,4,6,7-Tetrahydro-3-[N'-(3-methoxyphenyl)-ureido]-4-oxo-1-phenylpyrrolo[3,2,1-jk][1,4]benzodiazepine.

mp: 247°–248° C.

IR (Nujol): 3260, 1670, 1640, 1555, 1515, 1220, 1150, 1040 cm$^{-1}$.

NMR (DMSO-d$_6$, δ): 2.7–3.3 (2H, m), 3.5 (3H, s), 3.6–3.9 (1H, m), 4.1–4.5 (1H, m), 4.95 (1H, d, J=8 Hz), 6.2–7.6 (13H, m), 8.85 (1H, br s).

MASS: m/e=426 (M$^+$).

Example 12

(1) To a solution of (3S)-3-amino-3,4,6,7-tetrahydro-4-oxo-1-phenylpyrrolo[3,2,1-jk][1,4]benzodiazepine (0.97 g), indole-2-carboxylic acid (0.564 g), 1-hydroxybenzotriazole (472.5 mg) in N,N-dimethylformamide (10 ml) were added N-ethyl-N'-(3-dimethylaminopropyl)-carbodiimide hydrochloride (669.2 mg) and triethylamine (351.2 mg) under stirring at ambient temperature. The mixture was stirred for two hours under the same conditions. To the reaction mixture was added ethyl acetate. The mixture was washed with water, an aqueous solution of sodium bicarbonate and water. The organic layer was separated and dried over magnesium sulfate. Removal of the solvent afforded an amorphous material (1.55 g), which was chromatographed on silica gel with a mixture of chloroform and ethyl acetate (10:1) as an eluent to give an amorphous substance (1.39 g). This substance was triturated in diisopropyl ether and the resultant white powder was collected by filtration. The powder was stirred in water for 2 days, collected again and dried under reduced pressure and heating to give (3S)-3,4,6,7-tetrahydro-3-(2-indolylcarbonylamino)-4-oxo-1-phenylpyrrolo[3,2,1-jk][1,4]benzodiazepine (optical purity: 98.4% e.e.) (1.12 g).

mp: 177°–180° C.

IR (Nujol): 3230, 1675, 1638, 1600, 1530, 1445, 1372, 1300, 1235, 1110, 745 cm$^{-1}$.

NMR (CDCl$_3$, δ): 3.0–3.5 (2H, m), 3.8–4.2 (1H, m), 4.5–4.85 (1H, m), 5.68 (1H, d, J=7.5 Hz), 7.0–7.8 (13H, m), 8.07 (1H, d, J=7.5 Hz), 9.90 (1H, br s).

MASS: m/e=420 (M$^+$).

$[\alpha]_D^{20}$=−63.8° (c=0.5, CHCl$_3$).

The following compounds were obtained according to a similar manner to that of Example 12(1).

(2) (3R)-3,4,6,7-Tetrahydro-3-(2-indolylcarbonylamino)-4-oxo-1-phenylpyrrolo[3,2,1-jk][1,4]benzodiazepine (optical purity: 97.74% e.e).

mp: 171°–177° C. (dec.).

IR (Nujol): 3230, 1674, 1638, 1600, 1530, 1445, 1370, 1300, 1236, 1112, 745, 695 cm$^{-1}$.

NMR (CDCl$_3$, δ): 3.0–3.5 (2H, m), 3.8–4.16 (1H, m), 4.5–4.82 (1H, m), 5.67 (1H, d, J=7.5 Hz), 7.0–7.75 (13H, m), 8.08 (1H, d, J=7.5 Hz), 9.95 (1H, br s).

MASS: m/e=420 (M$^+$).

$[\alpha]_D^{20}$=64.88° (c=0.524, CHCl$_3$).

(3) (3S)-1-(2-Fluorophenyl)-3,4,6,7-tetrahydro-3-(2-indolylcarbonylamino)-4-oxopyrrolo[3,2,1-jk][1,4]-benzodiazepine (optical purity: 97.8% e.e.).

mp: 270°–275° C.

NMR (DMSO-d$_6$, δ): 3.0–3.65 (2H, m), 3.75–4.20 (1H, m), 4.30–4.70 (1H, m), 5.55 (1H, d, J=8 Hz), 6.90–7.75 (12H, m), 9.53 (1H, d, J=8 Hz), 11.65 (1H, br s).

MASS: m/e=438 (M$^+$).

$[\alpha]_D^{25}$=19.8° (c=0.3, CHCl$_3$).

(4) (3R)-1-(2-Fluorophenyl)-3,4,6,7-tetrahydro-3-(2-indolylcarbonylamino)-4-oxopyrrolo[3,2,1-jk][1,4]-benzodiazepine (optical purity: 93.4% e.e.).

mp: 260°–265° C. (dec.).

NMR (DMSO-d$_6$, δ): 3.0–3.65 (2H, m), 3.75–4.20 (1H, m), 4.30–4.70 (1H, m), 5.55 (1H, d, J=8 Hz), 6.90–7.75 (12H, m), 9.53 (1H, d, J=8 Hz), 11.63 (1H, br s).

MASS: m/e=438 (M$^+$).

$[\alpha]_D^{25}$=−17.8° (c=0.3, CHCl$_3$).

Example 13

The following compound was obtained according to a similar manner to that of Example 2(1).

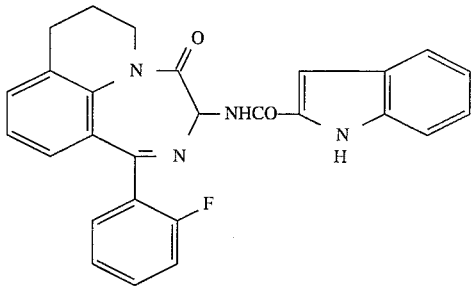

(3RS)-1-(2-Fluorophenyl)-3,4,7,8-tetrahydro-3-(2-indolylcarbonylamino)-4-oxo-6H-pyrido[3,2,1-jk][1,4]-benzodiazepine.

NMR (DMSO-d$_6$, δ): 1.55–2.25 (2H, m), 2.75–3.30 (3H, m), 4.15–4.55 (1H, m), 5.53 (1H, d, J=8 Hz), 6.85–7.70 (12H, m), 9.40 (1H, d, J=8 Hz).

MASS: m/e=452 (M$^+$).

Preparation 12

A mixture of 7-cyanoindoline (4.32 g) and 50% aqueous sulfuric acid (40 ml) was stirred at 110°–120° C. for 5.5 hours, cooled to 5° C. and adjusted to pH 7–8 with 24% aqueous sodium hydroxide. The mixture was washed with ethyl acetate and the aqueous layer was adjusted to pH 2.5–3.0 with 6N hydrochloric acid. The precipitates were collected by filtration to give indoline-7-carboxylic acid (3.25 g).

IR (Nujol): 3420, 2600, 1650, 1605, 1590 cm$^{-1}$.

NMR (CDCl$_3$, δ): 3.07 (2H, tri, J=18 Hz), 3.74 (2H, tri, J=18 Hz), 6.53–6.60 (1H, m), 7.17–7.25 (1H, m), 7.59–7.63 (1H, m).

Preparation 13

A solution of methyl (E)-3-(2-aminophenyl)propenoate (531.6 mg) and 4-formylimidazole (317.1 mg) in methanol (7.0 ml) was stirred at ambient temperature for 18 hours. To the reaction mixture was added sodium borohydride (56.5 mg) under stirring and cooling in an ice-bath. After the mixture was stirred for 2 hours at ambient temperature, sodium borohydride (56.5 mg) was added thereto. The mixture was stirred for 2 hours at ambient temperature. To the reaction mixture was added acetic acid in order to decompose the excess sodium borohydride and the methanol was removed under reduced pressure. To the residue were added diluted hydrochloric acid and ethyl acetate under stirring. The separated aqueous layer was basified with aqueous sodium bicarbonate and extracted twice with ethyl acetate. The extract was washed with water, dried over magnesium sulfate and evaporated to give a residue, which was subjected to column chromatography on silica gel with an eluent of a mixture of chloroform and methanol (20:1) to afford pure methyl (E)-3-[2-(4-imidazolylmethylamino)phenyl]-propenoate (0.7 g) as an oil.

NMR (CDCl$_3$, δ): 3.75 (3H, s), 4.33 (2H, s), 4.51 (1H, broad), 6.31 (1H, d, J=15.7 Hz), 6.68–7.58 (6H, m), 7.81

(1H, d, J=15.7 Hz).

Preparation 14

To a solution of methyl (E)-3-[2-(4-imidazolylmethylamino)phenyl]propenoate (0.7 g) in methanol (7 ml) was added 1N sodium hydroxide aqueous solution (3 ml) and the mixture was stirred for 20 hours. After removal of methanol from the reaction mixture, water was added to the residue. The mixture was adjusted to pH 6 with acetic acid. The mixture was salted out and extracted with ethyl acetate 8 times. The extracts were combined and dried over magenessium sulfate. Removal of the solvent afforded an orange oil, which was dissolved in methanol (5 ml). To the solution was added an ethereal solution of hydrogen chloride. The resultant precipitate was collected by filtration, washed with ether twice and dried to give (E)-3-[2-(4-imidazolylmethylamino)phenyl]propenoic acid dihydrochloride (0.29 g).

NMR ($D_2O$, δ): 4.65 (2H, S), 6.38 (1H, d, J=15.6 Hz), 7.02–7.6 (5H, m), 7.80 (1H, d, J=15.6 Hz), 8.67 (1H, s).

Example 14

The following compounds were obtained according to a similar manner to that of Example 2(1).

(1) (3RS)-3,4,6,7-Tetrahydro-1-(2-fluorophenyl)-3-[(E)-3-{2-(4-imidazolylmethylamino)phenyl}-propenoylamino]-4-oxopyrrolo[3,2,1-jk][1,4]-benzodiazepine mp: 205°–210° C. (dec.).

IR (Nujol): 3200, 2600, 1691, 1645, 1610, 1600, 1540, 1505 $cm^{-1}$

NMR ($CDCl_3$, δ): 3.02–3.34 (2H, m), 3.85–4.01 (1H, m), 4.30 (2H, s), 4.53–4.63 (2H, m), 5.54 (1H, d, J=7.4 Hz), 6.49 (1H, d, J=15 Hz), 6.68–7.63 (14H, m), 7.76 (1H, d, J=7.4 Hz), 7.78 (1H, d, J=15 Hz).

(2) (3RS)-3,4,6,7-Tetrahydro-1-(2-fluorophenyl)-3-(7-indolinylcarbonylamino)-4-oxo-pyrrolo [3,2,1-jk]-[1,4]benzodiazepine.

mp: 165°–170° C. (dec.).

IR (Nujol): 3310, 1665, 1630, 1590, 1522 $cm^{-1}$.

NMR ($CDCl_3$, δ): 3.04 (2H, tri, J=8.4 Hz), 3.14–3.20 (1H, m), 3.28–3.46 (1H, m), 3.67 (2H, tri, J=8.4 Hz), 3.96–4.12 (1H, m), 4.61–4.73 (1H, m), 5.62 (1H, d, J=7.4 Hz) 6.29 (1H, bs), 6.58–6.66 (1H, m), 6.98–7.71 (9H, m), 7.92 (1H, d, J=7.4 Hz).

MASS: m/e=440 ($M^+$).

(3) (3RS)-3,4,6,7-Tetrahydro-1-(2-fluorophenyl)-3-(quinolylcarbonylamino)-4-oxo-pyrrolo[3,2,1-jk][1,4]benzodiazepine hydrochloride.

mp: 198°–200° C.

IR (Nujol): 3550–3100, 2700–2100, 1660, 1605, 1520 $cm^{-1}$.

NMR ($CDCl_3$, δ): 3.07–3.55 (2H, m), 3.95–4.2 (1H, m), 4.6–4.8 (1H, m), 5.83 (1H, d, J=7.3 Hz), 7.00–7.27 (4H, m), 7.51–7.69 (3H, m), 7.85–7.92 (1H, m), 8.04–8.11 (1 H, m), 8.26 (1H, d, J=8 Hz), 8.84 (1H, d, J=8.5 Hz), 9.47 (1H, d, J=7 Hz), 9.60 (1H, s), 9.79 (1H, s).

(4) (3RS)-3,4,6,7-Tetrahydro-1-(2-fluorophenyl)-3-[(E)-3-(8-quinolyl)propenoylamino]-4-oxopyrrolo-[3,2,1-jk][1,4]benzodiazepine hydrochloride.

mp: 180°–185° C.

IR (Nujol): 3280, 1668, 1647, 1623, 1540, 1450, 1372, 1212, 981, 767, 748 $cm^{-1}$.

NMR (DMSO-$d_6$, δ): 3.11–3.49 (2H, m), 3.99 (1H, q, J=10.8 Hz), 4.52 (1H, t, J=9.8 Hz), 5.47 (1H, d, J=8.2 Hz), 7.0–9.0 (15H, m).

(5) (3S)-3,4,6,7-Tetrahydro-1-(2-fluorophenyl)-3-[(2-amino-4-chlorobenzoyl)amino]-4-oxopyrrolo[3,2,1-jk][1,4]benzodiazepine.

mp: 217°–220° C.

IR (Nujol): 3400, 3300, 1675, 1630, 1610 $cm^{-1}$.

NMR ($CDCl_3$, δ): 3.09–3.46 (2H, m), 3.97–4.12 (1H, m), 4.61–4.73 (1H, m), 5.58 (1H, d, J=7.3 Hz), 5.69 (2H, bs), 6.64–7.88 (1H, m),

MASS: m/e=448 ($M^+$).

$[α]_D^{25}$=−60.59° (C=0.812, $CHCl_3$).

(6) (3S)-3,4,6,7-Tetrahydro-1-(2-fluorophenyl)-3-[(E)-3-(2-hydroxphenyl)propenoylamino]-4-oxopyrrolo[3,2,1-jk][1,4]benzodiazepine.

m.p.: 178°–192° C. (dec.).

IR (Nujol): 3400–3000, 1650, 1600 $cm^{-1}$.

NMR ($CDCl_3$, δ): 3.09–3.47 (2H, m), 3.97–4.12 (1H, m), 4.63–4.73 (1H, m), 5.65 (1H, d, J=8 Hz), 6.76–7.72 (13H, m), 7.98 (1H, d, J=16 Hz), 8.76 (1H, s).

MASS: m/e=441 ($M^+$).

$[α]_D^{25}$=23.17° (C=0.902 MeOH).

(7) (3S)-3,4,6,7-Tetrahydro-1-(2-fluorophenyl)-3-[(E)-3-(2-nitrophenyl)propenoylamino]-4-oxopyrrolo[3,2,1-jk][1,4]benzodiazepine.

m.p.: 215°–220° C. (dec.).

IR (Nujol): 3300, 1670, 1650, 1630, 1550, 1520 $cm^{-1}$.

NMR ($CDCl_3$, δ): 3.15–3.47 (2H, m), 3.96–4.12 (1H, m), 4.61–4.72 (1H, m), 5.6 (1H, d, J=7.8 Hz), 6.56 (1H, d, J=15.5 Hz), 6.99–8.17 (13H, m).

(8) (3RS)-3,4,6,7-Tetrahydro-1-(2-fluorophenyl)-3-[(E)-3-(4-chlorophenyl)propenoylamino]-4-oxopyrrolo[3,2,1-jk][1,4]benzodiazepine.

m.p: 153°–160° C. (dec.).

IR (Nujol): 3300, 1675, 1650, 1620, 1520 $cm^{-1}$.

NMR ($CDCl_3$, δ): 3.09–3.57 (2H, m), 3.97–4.72 (1H, m), 4.60–4.72 (1H, m), 5.59 (1H, d, J=8 Hz), 6.61 (1H, d, J=16 Hz), 6.99–7.71 (13H, m).

MASS: m/e=459 ($M^+$).

(9) (3RS)-3,4,6,7-Tetrahydro-1-(2-fluorophenyl)-3-[(N-phenylglycyl)amino]-4-oxopyrrolo-[3,2,1-jk]-[1,4]benzodiazepine.

m.p: 135°–137° C. (dec.).

IR (Nujol): 3450, 3125, 1675, 1650, 1600, 1530 $cm^{-1}$.

NMR ($CDCl_3$, δ): 3.06–3.18 (2H, m), 3.89–4.07 (1H, m), 4.57–4.68 (1H, m), 5.48 (1H, d, J=8 Hz), 6.7–7.65 (15H, m), 8.21 (1H, d, J=8 Hz).

MASS: m/e=4.28 ($M^+$).

(10) (3RS)-3,4,6,7-Tetrahydro-1-(2-fluorophenyl)-3-[(E)-3-(4-fluorophenyl)propenoylamino]-4-oxopyrrolo[3,2,1-jk][1,4]benzodiazepine.

m.p: 186°–193° C.

NMR ($CDCl_3$, δ): 3.09–3.47 (2H, m), 3.95–4.11 (1H, m), 4.6–4.73 (1H, m), 5.59 (1H, d, J=8 Hz), 6.56 (1H, d, J=16 Hz), 6.99–7.7 (13H, m).

MASS: m/e=443 ($M^+$).

(11) (3RS)-3,4,6,7-Tetrahydro-1-(2-fluorophenyl)-3-[(E)-3-(4-nitrophenyl)propenoylamino]-4-oxopyrrolo[3,2,1-jk][1,4]benzodiazepine.

m.p.: 267°–269° C.

IR (Nujol): 3300, 1650, 1630, 1595, 1530, 1510 $cm^{-1}$.

NMR (CDCl₃, δ): 3.19–3.4 (2H, m), 4.02–4.08 (1H, m), 4.62–4.72 (1H, m), 5.58 (1H, d, J=8 Hz), 6.72 (1H, d, J=16 Hz), 7.0–7.78 (12H, m), 8.26 (1H, d, J=9 Hz).

MASS: m/e=470 (M⁺).

(12) (3RS)-3,4,6,7-Tetrahydro-1-(2-fluorophenyl)-3-[(E)-3-(4-methylphenyl)propenoylamino]-4-oxopyrrolo[3,2,1-jk][1,4]benzodiazepine.

m.p.: 224°–225° C.

IR (Nujol): 3250, 1680, 1650, 1600, 1520 cm⁻¹.

NMR (CDCl₃, δ): 2.37 (3H, s), 3.08–3.46 (2H, m), 3.95–4.11 (1H, m), 4.61–4.71 (1H, m), 5.6 (1H, d, J=8 Hz), 6.59 (1H, d, J=16 Hz), 6.98–7.72 (13H, m).

MASS: m/e=439 (M⁺).

(13) (3RS)-3,4,6,7-Tetrahydro-1-(2-fluorophenyl)-3-[(E)-3-(3,4-dichlorophenyl)propenoylamino]-4-oxopyrrolo[3,2,1-jk][1,4]benzodiazepine.

m.p: 250°–252° C.

IR (Nujol): 3270, 1670, 1650, 1620, 1540 cm⁻¹.

NMR (CDCl₃, δ): 3.10–3.47 (2H, m), 3.96–4.11 (1H, m), 4.61–4.71 (1H, m), 5.57 (1H, d, J=8 Hz), 6.62 (1H, d, J=16 Hz), 6.99–7.69 (12H, m).

MASS: m/e=493 (M⁺).

(14) (3RS)-3,4,6,7-Tetrahydro-1-(2-fluorophenyl)-3-[(E)-3-(4-methoxyphenyl)propenoylamino]-4-oxopyrrolo[3,2,1-jk][1,4]benzodiazepine.

m.p: 230°–233° C.

IR (Nujol): 3350, 1655, 1625, 1600, 1510 cm⁻¹.

NMR (CDCl₃, δ): 3.08–3.46 (2H, m), 3.84 (3H, s), 3.95–4.11 (1H, m), 4.61–4.71 (1H, m), 5.60 (1H, d, J=8 Hz), 6.5 (2H, d, J=16 Hz), 6.89–7.71 (13H, m).

MASS: m/e=455 (M⁺).

(15) (3RS)-3,4,6,7-Tetrahydro-1-(2-fluorophenyl)-3-[(E)-3-(2-chlorophenyl)propenoylamino]-4-oxopyrrolo[3,2,1-jk][1,4]benzodiazepine.

m.p: 137°–140° C. (dec.).

IR (Nujol): 3250, 1670, 1650, 1635, 1540 cm⁻¹.

NMR (CDCl₃, δ): 3.09–3.47 (2H, m), 3.95–4.11 (1H, m), 4.61–4.73 (1H, m), 5.6 (1H, d, J=8 Hz), 6.6–6.67(1H, d, J=16 Hz), 6.98–7.71 (12H, m), 8.09 (1H, d, J=16 Hz).

MASS: m/e=459 (M⁺).

(16) (3RS)-3,4,6,7-Tetrahydro-1-(2-fluorophenyl)-3-[(E)-3-(3-chlorophenyl)propenoylamino]-4-oxopyrrolo[3,2,1-jk][1,4]benzodiazepine.

m.p: 130°–135° C. (dec.).

IR (Nujol): 3350–3100, 1690, 1660, 1630 cm⁻¹.

NMR (CDCl₃, δ): 3.09–3.47 (2H, m), 3.95–4.11 (1H, m), 4.61–4.77 (1H, m), 5.58 (1H, d, J=8 Hz), 6.64 (1H, d, J=16 Hz), 6.99–7.67 (13H, m).

MASS: m/e=459(M⁺).

(17) (3RS)-3,4,6,7-Tetrahydro-1-(2-fluorophenyl)-3-[(E)-3-(2-nitrophenyl)propenoylamino]-4-oxopyrrolo[3,2,1-jk][1,4]benzodiazepine.

m.p: 170°–185° C. (dec.).

IR (Nujol): 3260, 1670 cm⁻¹.

NMR (CDCl₃, δ): 3.09–3.47 (2H, m), 3.94–4.11 (1H, m), 4.61–4.72 (1H, m), 5.60 (1H, d, J=8 Hz), 6.57 (1H, d, J=15 Hz), 6.99–7.72 (11H, m), 8.02–8.17 (2H, m).

(18) (3RS)-3,4,6,7-Tetrahydro-1-(2-fluorophenyl)-3-[(E)-3-(3,4-dihydroxyphenyl)propenoylamino]-4-oxopyrrolo[3,2,1-jk][1,4]benzodiazepine.

IR (Nujol): 3550–3000, 1650, 1600, 1510 cm⁻¹.

NMR (CDCl₃, δ): 3.09–3.46 (2H,m), 3.90–4.00 (1H, m) 4.44–4.54 (1H, m), 5.41 (1H, d, J=8 Hz), 5.43–6.50 (1H, b), 6.98–7.61 (9H, m), 8.01 (1H, s), 9.25 (1H, s), 9.69 (1H, d, J=8 Hz).

(19) (3RS)-3,4,6,7-Tetrahydro-1-(2-fluorophenyl)-3-[(E)-3-(4-imidazolyl)propenoylamino]-4-oxopyrrolo[3,2,1-jk][1,4]benzodiazepine hydrochloride.

IR (Nujol): 3650–3100, 2750–2200, 1670, 1630, 1600, 1500 cm⁻¹.

NMR (DMSO-d₆, δ): 3.09–3.46 (2H, m), 3.90–4.00 (1H, m), 4.44–4.54 (1H, m), 5.41 (1H, d, J=8 Hz), 5.43–6.50 (1H, b), 6.98–7.61 (9H, m), 8.01 (1H, s), 9.25 (1H, s), 9.69 (1H, d, J=8 Hz).

(20) (3RS)-3,4,6,7-Tetrahydro-1-(2-fluorophenyl)-3-[(E)-3-(2-aminophenyl)propenoylamino]-4-oxopyrrolo[3,2,1-jk][1,4]benzodiazepine.

IR (Nujol): 3400, 3350, 3125, 1690, 1640, 1600, 1540 cm⁻¹.

(21) (3S)-3,4,6,7-Tetrahydro-1-(2-fluorophenyl)-3-[(E)-3-(2-aminophenyl)propenoylamino]-4-oxopyrrolo[3,2,1-jk][1,4]benzodiazepine.

IR (Nujol): 3280, 1670, 1645, 1615, 1545 cm⁻¹.

(22) (3RS)-3,4,6,7-Tetrahydro-1-(2-fluorophenyl)-3-[(E)-3-(4-aminophenyl)propenoylamino]-4-oxopyrrolo[3,2,1-jk][1,4]benzodiazepine.

IR (Nujol): 3250, 1675, 1640, 1580, 1530 cm⁻¹.

(23) (3RS)-3,4,6,7-Tetrahydro-1-(2-fluorophenyl)-3-[(E)-3-(2-carboxyindol-3-yl)propenoylamino]-4-oxopyrrolo[3,2,1-jk][1,4]benzodiazepine.

IR (Nujol): 3250, 1700 (sh), 1675, 1645, 1610, 1525, 1450, 1370, 1205, 985, 835, 745 cm⁻¹.

(24) (3S)-3,4,6,7-Tetrahydro-1-(2-fluorophenyl)-3-[[3-[(4-(2-hydroxyethyl)piperazin-1-yl]methyl]indol-2-yl]carbonylamino]-4-oxopyrrolo[3,2,1-jk][1,4]-benzodiazepine.

IR (Nujol): 3250, 1690, 1620, 1450, 1372, 1141, 1050, 740 cm⁻¹.

(25) (3S)-3,4,6,7-Tetrahydro-1-(2-fluorophenyl)-3-[[3-(N,N-dimethylaminomethyl)indol-2-yl]carbonylamino]-4-oxopyrrolo[3,2,1-jk][1,4]-benzodiazepine hydrochloride.

NMR (DMSO-d₆, δ): 2.72–2.78 (6H, m), 3.17–3.43 (2H, m), 4.02 (1H, q, J=10.8 Hz), 4.52 (1H, t, J=11.4 Hz), 4.74 (2H, ABq), 5.59 (1H, d, J=7.7 Hz), 7.1–8.0 (11H, m), 9.41 (1H, broad s), 9.83 (1H, d, J=7.7 Hz).

(26) (3RS)-3,4,6,7-Tetrahydro-1-(2-fluorophenyl)-3-[(E)-3-(2-acetamidophenyl)propenoylamino]-4-oxopyrrolo[3,2,1-jk][1,4]benzodiazepine.

NMR (CDCl₃, δ): 2.21 (3H, s), 3.07–3.36 (2H, m), 3.92–4.08 (1H, m), 4.58–4.69 (1H, m), 5.52 (1H, d, J=8 Hz), 6.56 (1H, d, J=15 Hz), 6.99–7.89 (13H, m).

(27) (3RS)-3,4,6,7-Tetrahydro-1-(2-fluorophenyl)-3-[(3-formylindol-2-yl)carbonylamino]-4-oxopyrrolo[3,2,1-jk][1,4]benzodiazepine.

IR (Nujol): 3200, 1678, 1640, 1580, 1445, 748 cm⁻¹.

(28) (3RS)-3,4,6,7-Tetrahydro-1-(2-fluorophenyl)-3-[(3-hydroxyiminomethylindol-2-yl)carbonylamino]-4-oxopyrrolo[3,2,1-jk][1,4]benzodiazepine.

NMR (DMSO-d₆, δ): 3.1–3.5 (2H, m), 4.00 (1H, q, J=10 Hz), 4.53 (1H, t, J=10 Hz), 5.57 (1H, d, J=7.6 Hz), 7.05–8.6 (11H, m), 8.97 (1H, s), 10.07 (1H, d, J=7.6 Hz), 11.02 (1H, s), 12.16 (1H, s).

(29) (3RS)-3,4,6,7-Tetrahydro-1-(2-fluorophenyl)-3-[(E)-3-(2-aminophenyl)propenoylamino]-4-oxopyrrolo[3,2,1-jk][1,4]benzodiazepine hydrochloride.

IR (Nujol): 3600–3100, 2650–2100, 1670, 1610 cm$^{-1}$.

(30) (3S)-3,4,6,7-Tetrahydro-1-(2-fluorophenyl)-3-[(E)-3-(2-aminophenyl)propenoylamino]-4-oxopyrrolo[3,2,1-jk][1,4]benzodiazepine hydrochloride.

IR (Nujol): 3600–3100, 2600–2200, 1660, 1610 cm$^{-1}$.

Example 15

To a solution of (3RS)-3,4,6,7-tetrahydro-1-(2-fluorophenyl)-3-amino-4-oxopyrrolo[3,2,1-jk][1,4]-benzodiazepine (177.7 mg) in N,N-dimethylformamide (4 ml) were added (E)-3-(2-ethoxycarbonyl-3-indolyl)propenoic acid (156.0 mg), 1-hydroxybenzotriazole (81.4 mg), N-ethyl-N'-(3-dimethylaminopropyl)carbodiimide hydrochloride (115.4 mg) and triethylamine (60.9 mg) under stirring at ambient temperature. The mixture was stirred for 4 hours and allowed to stand overnight. The reaction mixture was poured into a mixture of ethyl acetate and water under stirring. The separated organic layer was washed with water twice and dried. The solvent was removed under reduced pressure to give an amorphous residue, which was subjected to column chromatography on silica gel with an eluent of a mixture of chloroform and methanol (100:1). The fractions containing the desired product were combined and evaporated to afford a glassy substance, which was pulverized in a mixture of diethyl ether and methanol. The powder was collected by filtration and dried under reduced pressure to give pure (3RS)-3,4,6,7-tetrahydro-1-(2-fluorophenyl)-3-[(E)-3-(2-ethoxycarbonylindol-3-yl)propenoylamino]-4-oxopyrrolo[3,2,1-jk][1,4]benzodiazepine (148.3 mg).

IR (Nujol): 3250, 3180, 1710, 1670, 1605, 1530, 1450, 1240, 1212, 740 cm$^{-1}$.

NMR (CDCl$_3$, δ): 1.42 (3H, t, J=7.1 Hz), 3.1–3.4 (2H, m), 4.03 (1H, q, J=10.9 Hz), 4.42 (2H, q, J=7.1 Hz), 4.66 (1H, t, J=10.9 Hz), 5.70 (1H, d, J=8.0 Hz), 6.84 (1H, d, J=16.0 Hz), 6.8–7.7 (11H, m), 8.00 (1H, d, J=8.0 Hz), 8.53 (1H, d, J=16 Hz), 9.66 (1H, s).

MASS: m/e=536 (M$^+$).

Example 16

The following compound was obtained according to a similar manner to that of Example 15. (3RS)-3,4,6,7-Tetrahydro-1-(2-fluorophenyl)-3-[(3-phenyliminomethylindol-2-yl)carbonylamino]-4-oxopyrrolo[3,2,1-jk][1,4]benzodiazepine.

NMR (CDCl$_3$, δ): 3.0–3.5 (2H, m), 3.8–4.2 (1H, broad q), 4.5–4.8 (1H, broad t), 5.74 (1H, d, J=7.5 Hz), 6.8–7.8 (16H, m), 8.0 (1H, d, J=7.5 Hz), 10.4 (1H, s), 10.9 (1H, broad s).

MASS: m/e=541 (M$^+$).

Example 17

To a solution of coumaric acid (0.68 g) and N-methylmorpholine (0.46 ml) in a mixture of methylene chloride and N,N-dimethylformamide (10:1, 52 ml) was added dropwise isobutyl chloroformate (0.54 ml) under stirring at –5° C. The mixture was stirred under the same condition for 15 minutes. A solution of (3RS)-3,4,6,7-tetrahydro-1-(2-fluorophenyl)-3-amino-4-oxopyrrolo[3,2,1jk][1,4]-benzodiazepine (1.0 g) in a mixture of methylene chloride and N,N-dimethylformamide (10:1, 9 ml) was added to the mixture under stirring at 0° C. The mixture was stirred for 1.5 hours at 0° C. and for 14.5 hours at ambient temperature. After removal of methylene chloride from the reaction mixture, a saturated aqueous solution of sodium bicarbonate (50 ml) and ethyl acetate (50 ml) were added to the residue under stirring. The separated organic layer was washed with water and dried over magnesium sulfate. Removal of the solvent gave an amorphous mass, which was subjected to column chromatography on silica gel eluting with a mixture of chloroform and methanol (50:1). The fractions containing the desired product were combined and evaporated. The residue was stirred in diisopropyl ether for several hours, collected by filtration, washed with diisopropyl ether and dried under reduced pressure to give (3RS)-3,4,6,7-tetrahydro-1-(2-fluorophenyl)-3-[(E)-3-(2-hydroxyphenyl)propenoylamino]-4-oxopyrrolo[3,2,1-jk][1,4]benzodiazepine (853.9 mg) as a white powder.

mp: 239°–241° C. (dec.).

IR (Nujol): 3325, 3200–3000, 1670, 1655, 1610, 1600, 1510 cm$^{-1}$.

NMR (CDCl$_3$, δ): 2.8–3.5 (2H, m), 3.8–4.3 (1H, m), 4.43–4.93 (1H, m), 5.62 (1H, d, J=8 Hz), 6.67–8.1 (14H, m), 8.57 (1H, bs).

MASS: m/e=441 (M$^+$)

Example 18

To a suspended mixture of iron powder (3.68 g) and ammonium chloride (0.44 g) in a mixture of water (9.2 ml) and ethanol (27.6 ml) was added portionwise (3RS)-3,4,6,7-tetrahydro-1-(2-fluorophenyl)-3-[(E)-3-(2-nitrophenyl)propenoylamino]-4-oxopyrrolo[3,2,1-jk][1,4]benzodiazepine (3.68 g) under stirring and refluxing. After additional ethanol (10 ml) and water (3.4 ml) were added to the mixture, the resultant mixture was refluxed under stirring for 2.5 hours. The reaction mixture was filtered through Celite and washed with hot ethanol several times. From the filtrate and the washings, ethanol was removed under reduced pressure. To the residual mixture was added a saturated aqueous solution of sodium bicarbonate (100 ml), and the mixture was extracted with chloroform. The extract was washed with water, dried over magnesium sulfate and evaporated to give a crystalline residue, which was pulverized with diisopropyl ether (100 ml) and collected by filtration to afford (3RS)-3,4,6,7-tetrahydro-1-(2-fluorophenyl)-3-[(E)-3-(2-aminophenyl)-propenoylamino]-4-oxopyrrolo[3,2,1-jk][1,4]benzodiazepine (1.56 g) as an yellow powder.

mp: 237°–240° C. (dec.).

IR (Nujol): 3400, 3350, 3125, 1690, 1640, 1600, 1540 cm$^{-1}$.

NMR (CDCl$_3$, δ): 3.08–3.45 (2H, m), 3.95–4.14 (3H, m), 4.60–4.71 (1H, m), 5.6 (1H, d, J=8 Hz), 6.51–7.87 (14H, m).

MASS: m/e=440 (M$^+$).

Example 19

The following compounds were obtained according to a similar manner to that of Example 18.

(1) (3S)-3,4,6,7-Tetrahydro-1-(2-fluorophenyl)-3-[(E)-3-(2-aminophenyl)propenoylamino]-4-oxopyrrolo[3,2,1-jk][1,4]benzodiazepine.

mp: 228°–230° C. (dec.).

IR (Nujol): 3280, 1670, 1645, 1615, 1545 cm$^{-1}$.

NMR (CDCl$_3$, δ): 3.08–3.45 (2H, m), 4.00 (2H, s), 3.94–4.10 (1H, m), 4.60–4.71 (1H, m), 5.06 (1H, d, J=7.9 Hz), 6.55 (1H, d, J=15.4 Hz), 6.67–7.68 (12H, m), 7.83 (1H, d, J=15.5 Hz).

$[\alpha]_D^{25}$=13.02° (C=0.86, CHCl$_3$).

MASS: m/e=440 (M$^+$).

(2) (3RS)-3,4,6,7-Tetrahydro-1-(2-fluorophenyl)-3-[(E)-3-(4-aminophenyl)propenoylamino]-4-oxopyrrolo[3,2,1-jk][1,4]benzodiazepine.

mp: 227°–228° C.

IR (Nujol): 3250, 1675, 1640, 1580, 1530 cm$^{-1}$.

NMR (CDCl$_3$, δ): 3.16–3.33 (4H, m), 4.00–4.10 (1H, m), 4.61–4.67 (1H, m), 5.61 (1H, d, J=7 Hz), 6.38–7.72 (14H, m).

MASS: m/e=440 (M$^+$).

Example 20

To 0.1N aqueous sodium hydroxide (7.5 ml) was dropwise added a suspension of (3RS)-3,4,6,7-tetrahydro-1-(2-fluorophenyl)-3-[(E)-3-(2-ethoxycarbonylindol-3-yl)propenoylamino]-4-oxopyrrolo[3,2,1-jk][1,4]benzodiazepine (268.3 mg) in 95% ethanol (10 ml) under stirring and refluxing. The resultant mixture was refluxed for 15 minutes. From the cooled reaction mixture, ethanol was removed under reduced pressure. To the residue was added water and the mixture was acidified with diluted hydrochloric acid. The mixture was extracted with ethyl acetate. The extract was washed with water twice and dried over magnesium sulfate. Removal of the solvent gave a crystalline powder, which was washed with diethyl ether under stirring and collected by filtration to give (3RS)-3,4,6,7-tetrahydro-1-(2-fluorophenyl)-3-[(E)-3-(2-carboxyindol-3-yl)-propenoylamino]-4-oxopyrrolo[3,2,1-jk][1,4]-benzodiazepine (192.0 mg).

mp: 215°–218° C. (dec.).

IR (Nujol): 3250, 1700 (sh), 1675, 1645, 1610, 1525, 1450, 1370, 1205, 985, 835, 745 cm$^{-1}$.

NMR (DMSO-d$_6$, δ): 3.1–3.4 (2H, m), 4.00 (1H, q, J=10.8 Hz), 4.51 (1H, t, J=10.8 Hz), 5.43 (1H, d, J=8 Hz), 7.0–7.6 (12H, m), 8.25 (1H, d, J=8 Hz), 8.47 (1H, d, J=16 Hz), 9.39 (1H, d, J=8 Hz), 12.14 (1H, s), 13.53 (1H, broad s).

Example 21

(1) To a solution of 1-(2-hydroxyethyl)piperazine (156.2 mg) and paraformaldehyde (37.9 mg) in acetic acid (4 ml) was added (3S)-3,4,6,7-tetrahydro-1-(2-fluorophenyl)-3-(2-indolylcarbonylamino)-4-oxopyrrolo[3,2,1-jk][1,4]-benzodiazepine (438.5 mg) under stirring at room temperature. The mixture was heated at about 85° C. for 3 hours. After removal of acetic acid, to the residue was added an aqueous solution of sodium bicarbonate and the mixture was extracted with ethyl acetate. The extract was washed with water twice and dried over magnesium sulfate. The solvent was removed under reduced pressure to give a viscous oil (0.68 g), which was chromatographed on silica gel with an eluent of a mixture of chloroform and methanol (50:1) to give colorless oil (494.5 mg). This oil was triturated in ether to give (3S)-3,4,6,7-tetrahydro-1-(2-fluorophenyl)-3-[[3-[(4-(2-hydroxyethyl)piperazin-1-yl)methyl]-indol-2-yl]carbonylamino]-4-oxopyrrolo[3,2,1-jk][1,4]-benzodiazepine.

IR (Nujol): 3250, 1690, 1620, 1450, 1372, 1141, 1050, 740 cm$^{-1}$.

NMR (CDCl$_3$, δ): 2.28 (2H, t, J=5.2 Hz), 2.53 (4H, br.s), 2.68 (4H, br.s), 3.07–3.19 (1H, m), 3.44 (2H, t, J=5.2 Hz), 3.2–3.5 (1H, m), 3.8–4.1 (3H, m), 4.6–4.7 (1H, m), 5.77 (1H, d, J=7Hz), 7.0–7.8 (12H, m), 9.79 (1H, s), 12.46 (1H, d, J=7.7 Hz).

MASS: m/e=580 (M$^+$).

(2) The compound obtained in Example 21(1) was treated with ethereal hydrogen chloride in methanol to give (3S)-3,4,6,7-tetrahydro-1-(2-fluorophenyl)-3-[[3-[(4-(2-hydroxyethyl)piperazin-1-yl)methyl]indol-2-yl]carbonylamino]-4-oxopyrrolo[3,2,1-jk][1,4]-benzodiazepine dihydrochloride (0.25 g).

mp: 225°–232° C.

$[\alpha]_D^{25}$: 13.0° (C=0.40, MeOH).

Example 22

(1) To a solution of N,N,N',N'-tetramethyldiaminomethane (143.1 mg) in dichloromethane (2 ml) was added dropwise acetyl chloride (109.9 mg) under cooling in an ice bath and stirring. The mixture was stirred under the same condition for one hour. To the resultant mixture was added (3S)-3,4,6,7-tetrahydro-1-(2-fluorophenyl)-3-(2-indolylcarbonylamino)-4-oxopyrrolo[3,2,1-jk][1,4]benzodiazepine (438.5 mg) under stirring at room temperature. The mixture was stirred for 4.5 hours at the same temperature. The solvent (dichloromethane) was removed by evaporation and to the residue was added water. The aqueous mixture was adjusted to pH 7.5–8 with a saturated aqueous solution of sodium bicarbonate and extracted with ethyl acetate twice and the extract was washed with water three times. After the extract was dried over magnesium sulfate, the solvent was removed under reduced pressure to afford viscous oil (0.61 g), which was purified by column chromatography on silica gel with an eluent of a mixture of chloroform and methanol (100:1) to give (3S)-3,4,6,7-tetrahydro-1-(2-fluorophenyl)-3-[[3-(N,N-dimethylaminomethyl)indol-2-yl]carbonylamino]-4-oxopyrrolo[3,2,1-jk][1,4]benzodiazepine (0.6 g).

(2) The compound obtained in Example 22 (1) was treated with ethereal hydrogen chloride in methanol to give (3S)-3,4,6,7-tetrahydro-1-(2-fluorophenyl)-3-[[3-(N,N-dimethylaminomethyl)indol-2-yl]carbonylamino]-4-oxopyrrolo[3,2,1-jk][1,4]benzodiazepine hydrochloride (0.52 g) as an yellow powder.

$[\alpha]_D^{25}$=83.0°(C=1.0, MeOH).

NMR (DMSO-d$_6$, δ): 2.72–2.78 (6H, m), 3.17–3.43 (2H, m), 4.02 (1H, q, J=10.8 Hz), 4.52 (1H, t, J=11.4 Hz), 4.74 (2H, ABq), 5.59 (1H, d, J=7.7 Hz), 7.1–8.0 (11H, m), 9.41 (1H, broad s), 9.83 (1H, d, J=7.7 Hz).

Example 23

To a suspended solution of (3RS)-3,4,6,7-tetrahydro-1-(2-fluorophenyl)-3-[(E)-3-(2-aminophenyl)-propenoylamino]-4-oxopyrrolo[3,2,1-jk][1,4]benzodiazepine (0.5 g) and dry pyridine (0.28 ml) in methylene chloride (15 ml) was added dropwise acetyl chloride (0.12 ml) under stirring and cooling in an ice-bath. The resultant clear solution was stirred for 0.5 hour under the same condition and for 2 hours at ambient temperature. The reaction mixture was washed with water, 1N hydrochloric acid and brine. The organic layer was dried over magnesium sulfate and evaporated under reduced pressure to give oil, which was chromatographed on silica gel eluting with a mixture of chloroform and methanol (50:1). The fractions containing the desired product were combined and evaporated. The residue was pulverized in diisopropyl ether, collected by filtration, washed with diisopropyl ether and dried under reduced pressure at 50° C. for 6 hours to give (3RS)-3,4,6,7-tetrahydro-1-(2-fluorophenyl)-3-[(E)-3-(2-acetamidophenyl)propenoylamino]-4-oxopyrrolo[3,2,1-jk][1,4]benzodiazepine (372 mg) as a white powder.

mp: 180°–189° C.

NMR (CDCl$_3$, δ): 2.21 (3H, s), 3.07–3.36 (2H, m), 3.92–4.08 (1H, m), 4.58–4.69 (1H, m), 5.52 (1H, d, J=8 Hz), 6.56 (1H, d, J=15 Hz), 6.99–7.89 (13H, m),

MASS: m/e=482 (M$^+$).

Example 24

To a suspension of (3RS)-3,4,6,7-tetrahydro-1-(2-fluorophenyl)-3-[(3-phenyliminomethylindol-2-yl)-carbonylamino]-4-oxopyrrolo[3,2,1-jk][1,4]benzodiazepine (1.73 g) in ethanol (30 ml) was added 2N hydrochloric acid (20 ml). The mixture was stirred under at 55° C. for 2 hours. The reaction mixture was cooled in an ice bath for 0.5 hour, and yellow precipitates were collected by filtration, washed with water and dried to give (3RS)-3,4,6,7-tetrahydro-1-(2-fluorophenyl)-3-[(3-formylindol-2-yl)carbonylamino]-4-oxopyrrolo[3,2,1-jk]-[1,4]benzodiazepine (1.44 g).

IR (Nujol): 3200, 1678, 1640, 1580, 1445, 748 cm$^{-1}$.

NMR (DMSO-d$_6$, δ): 3.1–3.5 (2H, m), 4.02 (1H, q, J=10 Hz), 4.53 (1H, t, J=10 Hz), 5.58 (1H, d, J=7.5 Hz), 7.05–8.3 (11H, m), 10.54 (1H, s), 11.30 (1H, d, J=7.5 Hz), 12.95 (1H, s).

MASS: m/e=466 (M$^+$).

Example 25

To a suspension of (3RS)-3,4,6,7-tetrahydro-1-(2-fluorophenyl)-3-[(3-formylindol-2-yl)carbonylamino]-4-oxopyrrolo[3,2,1-jk][1,4]benzodiazepine (466 mg) in glacial acetic acid (35 ml) were added successively hydroxylamine hydrochloride (208.5 mg) and sodium acetate (246.1 mg) under stirring at room temperature. The mixture was warmed under stirring at 70° C. for 8.5 hours and evaporated under reduced pressure. To the residue was added water and the resultant precipitates were collected by filtration and washed with water twice and cold methanol to give (3RS)-3,4,6,7-tetrahydro-1-(2-fluorophenyl)-3-[(3-hydroxyiminomethylindol-2-yl)-carbonylamino]-4-oxopyrrolo[3,2,1-jk][1,4]benzodiazepine (379.1 mg).

mp: >250° C.

NMR (DMSO-d$_6$, δ): 3.1–3.5 (2H, m), 4.00 (1H, q, J=10 Hz), 4.53 (1H, t, J=10 Hz), 5.57 (1H, d, J=7.6 Hz), 7.05–8.6 (11H, m), 8.97 (1H, s), 10.07 (1H, d, J=7.6 Hz), 11.02 (1H, s), 12.16 (1H, s).

MASS: m/e=481 (M$^+$).

Example 26

To a solution of (3RS)-3,4,6,7-tetrahydro-1-(2-fluorophenyl)-3-[(E)-3-(2-aminophenyl)propenoylamino]-4-oxopyrrolo[3,2,1-jk][1,4]benzodiazepine (0.5 g) in chloroform (30 ml) was added a mixture of 6N hydrochloric acid and ether (30 ml). The mixture was evaporated under reduced pressure. The residue was washed with ethanol three times and with diisopropyl ether once. The residue was pulverized in diisopropyl ether and the mixture was stirred for one hour. The resultant powder was collected by filtration, washed with diisopropyl ether and dried under reduced pressure to give (3RS)-3,4,6,7-tetrahydro-1-(2-fluorophenyl)-3-[(E)-3-(2-aminophenyl)propenoylamino]-4-oxopyrrolo[3,2,1-jk][1,4]benzodiazepine hydrochloride.

mp: 199°–203° C. (dec.).

IR (Nujol): 3600–3100, 2650–2100, 1670, 1610 cm$^{-1}$.

NMR (DMSO-d$_6$, δ): 3.1–3.63 (2H, m), 3.9–4.0 (1H, m), 4.45–4.55 (1H, m), 5.41 (1H, d, J=8 Hz), 7.04–7.78 (15H, m), 9.46 (1H, d, J=8 Hz).

MASS: m/e=440 (M$^+$-36).

Example 27

The following compound was obtained according to a similar manner to that of Example 26.

(3S)-3,4,6,7-Tetrahydro-1-(2-fluorophenyl)-3-[(E)-3-(2-aminophenyl)propenoylamino]-4-oxopyrrolo[3,2,1-jk][1,4]-benzodiazepine hydrochloride.

mp: 190°–195° C. (dec.).

IR (Nujol): 3600–3100, 2600–2200, 1660, 1610 cm$^{-1}$.

NMR (CDCl$_3$, δ): 3.18–3.46 (2H, m), 3.96–4.01 (1H, m), 4.44–4.54 (1H, m), 5.41 (1H, d, J=8 Hz), 7.04–7.78 (15H, m), 9.45 (1H, d, J=8 Hz), [α]$_D^{25}$: 46.81° (C=0.848, MeOH).

MASS: m/e=440 (M$^+$-36).

What we claim is:

1. A compound of the formula:

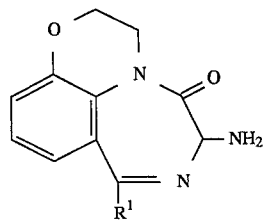

wherein

R$^1$ is aryl or substituted aryl, and a pharmaceutically acceptable salt thereof.

2. A compound of claim 1, wherein R$^1$ is phenyl which may have halogen.

3. (6RS)-6-Amino-2,3,5,6-tetrahydro-5-oxo-8-phenyl-1,4-oxazino[2,3,4-jk][1,4]benzodiazepine.

4. A cholecystokinin antagonist pharmaceutical composition which comprises, as an active ingredient, an effective amount of a compound of claim 1 or a pharmaceutically acceptable salt thereof in admixture with a pharmaceutically acceptable carrier.

5. A method for treating or preventing emesis or pancreatitis which comprises administering an effective amount of a compound of claim 1 or a pharmaceutically acceptable salt thereof to a human or animal.

* * * * *